(12) United States Patent
Bernstein et al.

(10) Patent No.: US 8,071,377 B2
(45) Date of Patent: Dec. 6, 2011

(54) METHODS FOR IMMORTALIZING CELLS

(75) Inventors: Irwin D. Bernstein, Seattle, WA (US);
Barbara Varnum-Finney, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 388 days.

(21) Appl. No.: 12/173,185

(22) Filed: Jul. 15, 2008

(65) Prior Publication Data
US 2009/0022696 A1     Jan. 22, 2009

Related U.S. Application Data

(63) Continuation of application No. 10/415,310, filed as application No. PCT/US01/48433 on Oct. 29, 2001, now Pat. No. 7,399,633.

(60) Provisional application No. 60/243,967, filed on Oct. 29, 2000.

(51) Int. Cl.
*C12N 5/02*     (2006.01)
(52) U.S. Cl. ........................................ 435/377; 435/372
(58) Field of Classification Search .................. None
See application file for complete search history.

(56) References Cited

OTHER PUBLICATIONS

Rizzino, Developmental Dynamics, vol. 236, pp. 3199-3207 (2007).*
Grafi, Trends in Biotechnology vol. 27, pp. 329-332 (2009).*

\* cited by examiner

*Primary Examiner* — Jim Ketter
(74) *Attorney, Agent, or Firm* — Christensen O'Connor Johnson Kindness PLLC

(57) ABSTRACT

The present invention provides methods for immortalizing precursor cells that are non-terminally differentiated cells such as stem cells, said methods comprising culturing the precursor cells in the presence of a Notch agonist and one or more growth factors that support the proliferation but not differentiation of the non-terminally differentiated cells. The present invention further provides methods to induce the differentiation of immortalized cells, comprising growing the cells in the presence of a Notch agonist and at least one growth factor which supports the differentiation of the cell into a more specialized cell type. The immortalized and/or differentiated cells of the invention can be used to repopulate cell populations that have been diminished, for example as a result of infection or exposure to certain drugs. The invention further provides a cell culture comprising a population of non-terminally differentiated cells immortalized by the methods of the present invention and kits comprising reagents that promote the immortalization of precursor cells. The invention further provides methods for screening for Notch modulators and for identifying genes involved in processes of cellular differentiation.

16 Claims, 9 Drawing Sheets

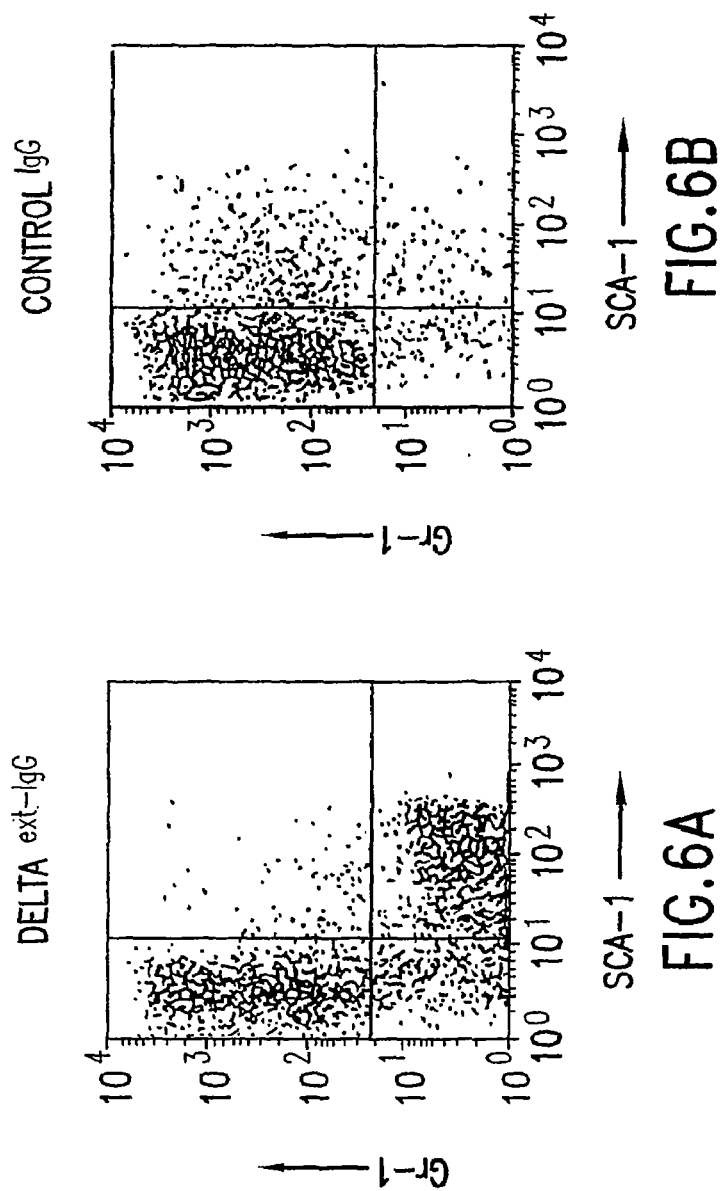

METHODS FOR IMMORTALIZING CELLS

CROSS-REFERENCE TO RELATED APPLICATIONS

Figure 1:
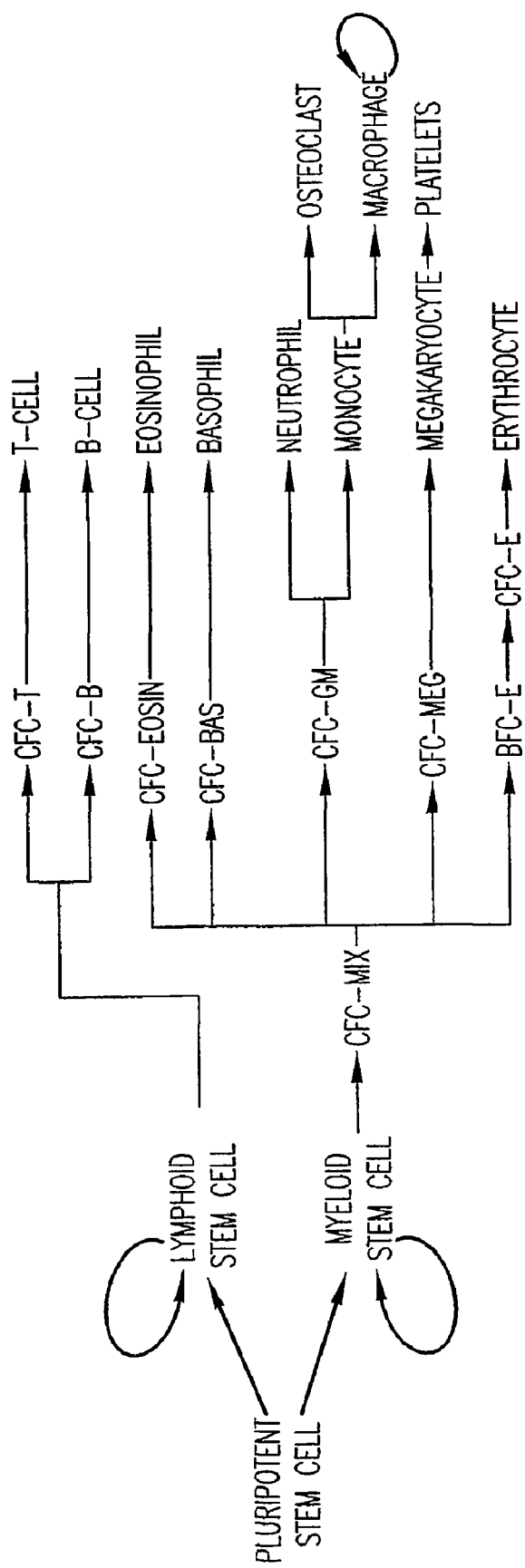

This application is a continuation of U.S. National Phase application Ser. No. 10/415,310, filed Sep. 29, 2003, now U.S. Pat. No. 7,399,633, issued Jul. 15, 2008, which is a National Phase Application under 35 U.S.C. §371 of Application No. PCT/US2001/48433, filed Oct. 29, 2001, which claims priority to U.S. Provisional Application No. 60/243,967, filed Oct. 29, 2000. All of these applications are incorporated herein by reference.

This invention was made with government support under grant number P50HL54881 awarded by the National Institutes of Health Heart and Lung Institute. The government has certain rights in the invention.

1 FIELD OF THE INVENTION

The present invention provides methods for producing immortalized precursor cell populations, said methods comprising culturing non-immortalized precursor cells in the presence of a Notch agonist and one or more proliferation-promoting growth factors for a time period beyond which cells of said precursor cell type stop proliferating and/or die. The invention further provides methods for producing immortalized and differentiated cell types comprising exposing precursor cells prior or following immortalization to conditions that promote their differentiation. Clonal cell lines can be established from the immortalized cells. The immortalized cells or clonal cell lines derived therefrom can be used for cell therapy. The present invention further provides methods for screening for Notch agonists and antagonists, and for identifying genes and gene products that are differentially expressed in the differentiation of precursor cells into more differentiated cell types.

2 BACKGROUND OF THE INVENTION

2.1 The Notch Signaling Pathway

Members of the Notch family encode large transmembrane proteins that play central roles in cell-cell interactions and cell-fate decisions during early development in a number of invertebrate systems (Simpson, 1995, Nature 375:736-7; Artavanis-Tsakonis et al., 1995, Science. 268:225-232; Simpson, 1998, Semin. Cell Dev. Biol. 9:581-2; Go et al., 1998, Development. 125:2031-2040; Artavanis-Tsakonas and Simpson, 1991, Trends Genet. 7:403-408). The Notch receptor is part of a highly conserved pathway that enables a variety of cell types to choose between alternative differentiation pathways based on those taken by immediately neighboring cells. This receptor appears to act through an undefined common step that controls the progression of uncommitted cells toward the differentiated state by inhibiting their competence to adopt one of two alternative fates, thereby allowing the cell either to delay differentiation, or in the presence of the appropriate developmental signal, to commit to differentiate along the non-inhibited pathway.

Genetic and molecular studies have led to the identification of a group of genes which define distinct elements of the Notch signaling pathway. While the identification of these various elements has come exclusively from *Drosophila* using genetic tools as the initial guide, subsequent analyses have lead to the identification of homologous proteins in vertebrate species including humans. The molecular relationships between the known Notch pathway elements as well as their subcellular localization are depicted in Artavanis-Tsakonas et al., 1995, Science 268:225-232) and Artvanis-Tsakonas et al., 1999, Science 284:770-776.

2.1.1 Members of the Notch Signaling Pathway

Several members of the Notch signaling pathway have been cloned and sequenced in invertebrate and vertebrate organisms. Non-mammalian Notch genes include those identified in *Drosophila* (Wharton et al., 1985, Cell 43:567-581); *Xenopus* (Coffman et al., 1990, Science 249:1438-1441); and zebrafish (Bierkamp et al., 1993, Mech. Dev. 43:87-100). At least four mammalian Notch homologs have been identified (Notch-1, -2, -3, and -4; Weinmaster et al., 1991, Development 113:199-205; Ellisen et al., 1991, Cell 66:523-534; Weinmaster et al., 1992, Development 116:931-941; Franco del Amo et al., 1993, Genomics 15:259-264; Lardelli and Lendahl, 1993, Exp. Cell. Res. 204:364-372; Milner et al., 1994, Blood. 83:2057-62; Lardelli et al., 1994, Mech Dev. 46:123-136; Uyttendaele et al., 1996, Development 122:2251-9). Other members of the Notch pathway include the ligands Delta and Serrate/Jagged, the cytoplasmic protein Deltex, the transcriptional activator RBP-Jκ, also known as CBF1, downstream targets including but not limited to the Enhancer of Split family of bHLH transcription factors, and, Fringe (Panin et al., 1997, Nature 387:908-912), which acts in the Golgi as a glycosyltransferase enzyme that modifies the epidermal growth factor (EGF) modules of Notch and alters the ability of Notch to bind its ligand Delta (Bruckner et al., 2000, Nature 406:411-415; see also Munro and Freeman, 2000, Curr. Biol. Jul 13; 10(14):813-820). The following non-exhaustive list of articles describes the gene and protein sequences, as well as functional roles, of key members of the Notch signaling pathway:

Invertebrate Ligands:
Delta: Kopczynski et al., 1988, Genes Dev. 2:1723-1735; Henrique et al., 1995, Nature 375:787-790; Chitnis et al., 1995, Nature 375:761-766.
Serrate: Fleming et al., 1990, Genes Dev. 1:2188-2201; Lindsell et al., 1995, Cell 80:909-917; Thomas et al., 1991, Development 111:749-761; Tax et al., 1994, Nature 368:150-154.

Vertebrate Ligands:
Serrate: Thomas, 1991, Development 111: 749-761; Lindsell et al., 1995, Cell 80:909-917.
Delta: Chitnis et al., 1995, Nature 375:761; Henrique et al., 1995, Nature 375:787-790; Bettenhausen et al., 1995, Development 121:2407).

Other Invertebrate Notch Pathway Members:
The cytoplasmic protein Deltex: Busseau et al., 1994, Genetics 136:585-596.
The nuclear proteins Mastermind, Hairless, the Enhancer of Split Complex: Smoller et al., 1990, Genes Dev. 4:1688-1700; Bang and Posakony, 1992, Genes Dev. 6:1752-1769; Maier et al., 1992, Mech. Dev. 38:143-156; Delidakis et al., 1991, Genetics 129:803-823; Schrons et al., 1992, Genetics 132:481-503; and Fortini and Artavanis-Tsakonas, 1994, Cell 79:273-282.
Suppressor of Hairless: Furukawa et al., 1991, J. Biol. Chem. 266:23334-23340; Furukawa et al., 1992, Cell 69:1191-1197; and Schweisguth and Posakony, 1992, Cell 69:1199-1212.
Fringe: Irvine and Wieschaus, 1994, Cell 79:595-606.

Other Vertebrate Notch Pathway Members:
RBP-Jκ: Matsunami et al., 1989, Nature 342:934-937; Kawaichi et al., 1992, J. Biol. Chem. 267:4016-4022.

Deltex: Matsunami et al., 1998, Nat. Genet. 19:74-78.

Fringe (including Lunatic, Manic and Radical Fringe): Wu et al., 1996, Science 273:355-358; Moran et al., 1999, Mamm. Genome 10:535-541.

2.1.2 Notch Family Members Encode Surface Receptors that Mediate Inhibitory Signals via the Cytoplasmic Domain Extensive genetic and molecular studies in *Drosophila* and *C. elegans* have shown that the proteins encoded by Notch homologs act as cell surface receptors which can activate inhibitory signal transduction pathways (Greenwald and Rubin, 1992, Cell. 68:271-281; Heitzler and Simpson, 1991, Cell 64:1083-1092; Yochem and Greenwald, 1989, Cell 58:553-63; Fehon et al., 1991, J. Cell Biol. 113:657-669; Rebay et al., 1993, Cell 74:319-329).

Notch signaling is thought to be initiated by interaction with one of the Notch ligands (Delta-1, -2, -3, or Jagged-1 or -2) (Shawber et al., 1996, Developmental Biology 180:370-76; Luo et al., 1997, Molecular and Cellular Biology 17:6057-6067; Henrique et al., 1997, Current Biology 7:661-70; Bettenhausen et al., 1995, Development 121:2407-18; Dunwoodie et al., 1997, Development 124:3065-76). Each of the known ligands is characterized by an extracellular domain containing multiple EGF repeats and a highly conserved DSL domain found in *Drosophila, C. elegans*, and in vertebrates (Tax et al., 1994, Nature 368:150-154). There is evidence that the ability of particular Notch ligands to induce Notch activation can be modified by the expression of other genes. For example, expression of Fringe prevents activation of Notch by Serrate (Drosophila homolog of Jagged), but enhances Delta activity (Fleming et al., 1997, Development 124:2973-81).

There is considerable evidence that cellular interactions mediated by the extracellular domain modulate signal transduction by the intracellular domain, resulting in regulation of differentiation (Yochem and Greenwald, 1989, Cell 58:553-563; Rebay et al., 1993, Cell 74:319-329). Recent data indicate that this occurs as a result of binding of the extracellular domain to one of its ligands, followed by a series of proteolytic cleavages which, in turn, leads to release of the intracellular domain of Notch (Struhl and Adachi, 1998, Cell. 93:649-660; Schroeter et al., 1998, Nature 393:382-386). Functional analyses involving the expression of truncated forms of the Notch receptor have indicated that receptor activation depends on the six cdc10/ankyrin repeats in the intracellular domain. Further, Notch activation requires that the cdc10/ankyrin repeats reach the nucleus—possibly after proteolytic cleavage from the remainder of the protein—and participate in transcriptional activation (Struhl and Adachi, 1998, Cell 93:649-660). Deltex and Suppressor of Hairless, whose over-expression results in an apparent activation of the pathway, associate with those repeats. Recent evidence suggests that the proteolytic cleavage step that releases the cdc10/ankyrin repeats for nuclear entry is dependent on Presenilin activity (De Strooper et al., 1999, Nature 398:518-522; Struhl and Greenwald, ibid.:522-525; Ye et al., ibid.: 525-529).

The Notch pathway is dependent on protein processing events additional to the step that releases the ankyrin repeats of Notch to the nucleus. The Notch receptor present in the plasma membrane comprises a heterodimer of two Notch proteolytic cleavage products, one comprising an N-terminal fragment consisting of a portion of the extracellular domain, the transmembrane domain and the intracellular domain, and the other comprising the majority of the extracellular domain (Blaumueller et al., 1997, Cell 0:281-291). The proteolytic cleavage step of Notch to activate the receptor occurs in the Golgi apparatus and is mediated by a furin-like convertase (Logeat et al., 1998, Proc. Natl. Acad. Sci. USA 95:8108-8112). The Notch ligand, Delta, additionally requires cleavage for activation. Delta is thought to be cleaved by a the ADAM disintegrin metalloprotease Kuzbanian at the cell surface to release a soluble and active form of Delta (Qi et al., 1999, Science 283:91-94).

This intracellular domain of Notch has been shown to act as a constitutively active receptor, since forced expression of this domain prevents myocyte fusion in C2 myoblasts (Kopan et al., 1994, Development 120:2385-2396), blocks muscle conversion of 3T3 cells by MyoD and Myf-5 (Kopan et al., 1994, Development 120:2385-2396), prevents muscle differentiation of DMSO-induced P19 embryonal carcinoma cells, and inhibits neurogenesis while permitting glial differentiation of P19 cells (Nye et al., 1994, Development 120:2421-2430).

This intracellular domain is thought to be transported to the nucleus where it appears to regulate transcription by interacting with a number of molecular targets, including CBF1/RBP-Jκ (Struhl and Adachi, 1998, Cell 93:649-660; Schroeter et al., 1998, Nature 393:382-386 Fortini et al., 1993, Nature 365:555-7). The downstream targets are not completely determined, but RBP-Jκ is known to activate expression of Hairy Enhancer of Split (HES) which functions as an inhibitor of transcriptional activity (Jarriault et al., 1998, Mol Cell Biol. 18:2230-9). RBP-Jκ, also known as CBF1, the homolog of the *Drosophila* gene Suppressor of Hairless, is a mammalian DNA binding protein involved in the Epstein-Barr virus-induced immortalization of B cells. It has been demonstrated that, at least in cultured cells, Suppressor of Hairless associates with the cdc10/ankyrin repeats in the cytoplasm and translocates into the nucleus upon the interaction of the Notch receptor with its ligand Delta on adjacent cells (Fortini and Artavanis, 1994, Cell 79:273-282). The association of Hairless, a novel nuclear protein, with Suppressor of Hairless has been documented using the yeast two hybrid system therefore, it is believed that the involvement of Suppressor of Hairless in transcription is modulated by Hairless (Brou et al., 1994, Genes Dev. 8:2491; Knust et al. 1992, Genetics 129:803). It is known that Notch signaling results in the activation of at least certain bHLH genes within the Enhancer of split complex (Delidakis et al., 1991, Genetics 129:803). Mastermind encodes a novel ubiquitous nuclear protein whose relationship to Notch signaling remains unclear but is involved in the Notch pathway as shown by genetic analysis (Smoller et al., 1990, Genes Dev. 4:1688).

There is also evidence that Notch signaling is mediated by an alternative, HES independent pathway, that involves signaling through Deltex and results in repression of E protein activity, e.g. in a B-cell system, it has also been shown that Deltex and not RBP-Jκ, is responsible for inhibiting E47 function (Ordentlich et al., 1998, Mol Cell Biol 18:2230-9). Deltex is a cytoplasmic protein which contains a ring zinc finger and interacts with the ankyrin repeats of Notch (Matsuno et al., 1995, Development 121:2633-2644).

2.1.3 Roles of Notch Family Members

U.S. Pat. No. 5,780,300 describes the roles of Notch proteins in differentiation processes. Briefly, Notch regulates the competence of many different cell types to respond to differentiation/proliferation/apoptosis signals, with the particular cell fates chosen depending upon the developmental history of each cell type and the specific signaling pathways operating within it. In *Drosophila* and *C. elegans*, members of the Notch/lin-12 family are required at multiple steps during the differentiation of a variety of tissues when specific cell fates are being determined. In *C. elegans*, the Notch-related genes lin-12 and glp-1 function in a wide variety of cell-cell interactions that result in the inhibition or expression of one or more potential cell fates (Greenwald and Rubin, 1992, Cell 68:271-81; Greenwald et al., 1983, Cell 34:435-444; Austin and Kimble, 1987, Cell 51:589-99; Yochem and Greenwald, 1989, Cell 58:553-563; Wilkinson et al., 1994, Cell 79:1187-1198). One particularly clear example is in the interactions involved in specifying cell fates in the developing vulva, wherein two equivalent multipotent precursors always from one anchor cell (AC) and one ventral uterine precursor (VU) cell (Greenwald and Rubin, 1992, Cell 68:271-81; Greenwald et al., 1983, Cell 34:435-44; Austin and Kimble, 1987, Cell 51:589-99; Yochem and Greenwald, 1989, Cell 58:553-63; Wilkinson et al., 1994, Cell 79:1187-98). If one of the stem cells is eliminated, the remaining cell always becomes an AC; if lin-12 activity is lacking, both become an AC; and if lin-12 activity is elevated, both cells express the VU fate. Further evidence indicates that a relative increase in expression of the ligand for lin-12, lag-2, in the cell committing to AC differentiation induces, via direct cell-cell interaction, an increase in lin-12 activity, which is inhibitory to AC differentiation but permissive for VU differentiation.

In *Drosophila*, Notch has been shown to be required for appropriate cell-fate decisions in numerous tissues, including the nervous system, eye, mesoderm, ovaries and other areas where multipotent progenitors are making cell-fate decisions (Artavanis-Tsakonas et al., 1999, Science 284:770-776; Go et al., 1998, Development 125:2031-2040; Doherty et al., 1996, Genes Dev. 10:421-434; Artavanis-Tsakonis et al., 1995, Science 268:225-232; Greenwald and Rubin, 1992, Cell 68:271-81; Heitzler and Simpson, 1991, Cell 64:1083-1092; Artavanis-Tsakonas and Simpson, 1991, Trends Genet. 7:403-408; Cagan and Ready, 1989, Genes Dev. 3:1099-1112). In the neurogenic region, for example, the differential expression of Notch appears to mediate a lateral inhibition in which a single cell within a cluster of equivalent cells adopts a neural fate while adjacent cells adopt epidermal fates. Similarly, in embryos with a homozygous null mutation of the Notch gene, all cells in the neurogenic region become neuroblasts and not epidermal precursors.

In *Xenopus*, the expression of mutant forms of Notch in developing embryos interferes profoundly with normal development (Coffman et al., 1993, Cell 73:659).

Studies of the expression of Notch-1, one of three known vertebrate homologs of Notch, in zebrafish and *Xenopus*, have shown that the general patterns are similar; with Notch expression associated in general with non-terminally differentiated, proliferative cell populations. Tissues with high expression levels include the developing brain, eye and neural tube (Coffman et al., 1990, Science 249:1438-1441; Bierkamp et al., 1993, Mech. Dev. 43:87-100). While studies in mammals have shown the expression of the corresponding Notch homologs to begin later in development, the proteins are expressed in dynamic patterns in tissues undergoing cell fate determination or rapid proliferation (Weinmaster et al., 1991, Development 113:199-205; Reaume et al., 1992, Dev. Biol. 154:377-387; Stifani et al., 1992, Nature Genet. 2:119-127; Weinmaster et al., 1992, Development 116:931-941; Kopan et al., 1993, J. Cell Biol. 121:631-641; Lardelli et al., 1993, Exp. Cell Res. 204:364-372; Lardelli et al., 1994, Mech. Dev. 46:123-136; Henrique et al., 1995, Nature 375: 787-790; Horvitz et al., 1991, Nature 351:535-541; Franco del Amo et al., 1992, Development 115:737-744). Among the tissues in which mammalian Notch homologs are first expressed are the pre-somitic mesoderm and the developing neuroepithelium of the embryo. In the pre-somitic mesoderm, expression of Notch-1 is seen in all of the migrated mesoderm, and a particularly dense band is seen at the anterior edge of pre-somitic mesoderm. This expression has been shown to decrease once the somites have formed, indicating a role for Notch in the differentiation of somatic precursor cells (Reaume et al., 1992, Dev. Biol. 154:377-387; Horvitz et al., 1991, Nature 351:535-541). Similar expression patterns are seen for mouse Delta (Simske et al., 1995, Nature 375: 142-145).

Within the developing mammalian nervous system, expression patterns of Notch homolog have been shown to be prominent in particular regions of the ventricular zone of the spinal cord, as well as in components of the peripheral nervous system, in an overlapping but non-identical pattern. Notch expression in the nervous system appears to be limited to regions of cellular proliferation, and is absent from nearby populations of recently differentiated cells (Weinmster et al., 1991, Development 113:199-205; Reaume et al., 1992, Dev. Biol. 154:377-387; Weinmaster et al., 1992, Development 116:931-941; Kopan et al., 1993, J. Cell Biol. 121:631-641; Lardelli et al., 1993, Exp. Cell Res. 204:364-372; Lardelli et al., 1994, Mech. Dev. 46:123-136; Henrique et al., 1995, Nature 375:787-790; Horvitz et al., 1991, Nature 351:535-541). A rat Notch ligand is also expressed within the developing spinal cord, in distinct bands of the ventricular zone that overlap with the expression domains of the Notch genes. The spatio-temporal expression pattern of this ligand correlates well with the patterns of cells committing to spinal cord neuronal fates, which demonstrates the usefulness of Notch as a marker of populations of cells for neuronal fates (Henrique et al., 1995, Nature 375:787-790). This has also been suggested for vertebrate Delta homologs, whose expression domains also overlap with those of Notch-1 (Larsson et al., 1994, Genomics 24:253-258; Fortini et al., 1993, Nature 365: 555-557; Simske et al., 1995, Nature 375: 142-145). In the cases of the *Xenopus* and chicken homologs, Delta is actually expressed only in scattered cells within the Notch-1 expression domain, as would be expected from the lateral specification model, and these patterns "foreshadow" future patterns of neuronal differentiation (Larsson et al., 1994, Genomics 24:253-258; Fortini et al., 1993, Nature 365:555-557).

Other vertebrate studies of particular interest have focused on the expression of Notch homologs in developing sensory structures, including the retina, hair follicles and tooth buds. In the case of the *Xenopus* retina, Notch-1 is expressed in the undifferentiated cells of the central marginal zone and central retina (Coffman et al., 1990, Science 249:1439-1441; Mango et al., 1991, Nature 352:811-815). Studies in the rat have also demonstrated an association of Notch-1 with differentiating cells in the developing retina have been interpreted to suggest that Notch-1 plays a role in successive cell fate choices in this tissue (Lyman et al., 1993, Proc. Natl. Acad. Sci. USA 90:10395-10399).

A detailed analysis of mouse Notch-1 expression in the regenerating matrix cells of hair follicles was undertaken to examine the potential participation of Notch proteins in epithelial/mesenchymal inductive interactions (Franco del Amo et al., 1992, Development 115:737-744). Such a role had originally been suggested for Notch-1 based on the its expression in rat whiskers and tooth buds (Weinmaster et al., 1991, Development 113:199-205). Notch-1 expression was instead found to be limited to subsets of non-mitotic, differentiating cells that are not subject to epithelial/mesenchymal interactions, a finding that is consistent with Notch expression elsewhere.

The human homolog of Notch-1 (TAN-1) was initially cloned from a T-cell leukemia with a translocation involving this gene and subsequently found in a variety of adult tissues, but in greatest amounts in thymus and lymph node (Ellisen et al., 1991, Cell 66:649-661; Zhong et al., 1997, Development 124:1887-1897; Vargesson et al., 1998, Mech Dev. 77:197-9; Lewis et al., 1998, Mech Dev. 78:159-163; Lindsell et al., 1996, Mol. Cell. Neurosci. 8:14-27; Hasserjian et al., 1996, Blood. 88:970-976). A homolog of Notch/TAN-1 is expressed in human CD34$^+$ hematopoietic precursors (Milner et al., 1994, Blood 83:2057-2062) as well as CD34$^-$ bone marrow cells (Milner et al., 1994, Blood 83:2057-2062; Varnum-Finney et al., 1998, Blood 91:4084-4091). Subsequent studies demonstrated widespread expression of Notch-1 and Notch-2 protein during hematopoietic development, as well as the Notch ligand, Jagged-1, in hematopoietic stroma (Varnum-Finney et al., 1998, Blood 91:4084-4091; Li et al., 1998, Immunity 8:43-55). The preferential expression of vertebrate Notch homologs in tissues undergoing cellular proliferation and differentiation suggests that these molecules are involved in mediating cell-fate decisions in vertebrates as they do in invertebrates. This persistence in tissues that are mitotically active also suggests that Notch may be involved in regulating cell proliferation. Consistent with this notion is the oncogenic phenotype associated with deregulated expression of the cytoplasmic domain of Notch-1 and, in mice, of the Notch-related int-3 locus which is a common integration site for mouse mammary tumor viruses in virus-induced tumors (Jhappan et al., 1992, Genes Dev. 6:345-355; Robbins et al., 1992, J. Virol. 66:2594-2599).

Additional studies of human Notch-1 and Notch-2 expression have been performed on adult tissue sections including both normal and neoplastic cervical and colon tissue. Notch-1 and Notch-2 appear to be expressed in overlapping patterns in differentiating populations of cells within squamous epithelia of normal tissues that have been examined and are clearly not expressed in normal columnar epithelia, except in some of the precursor cells. Both proteins are expressed in neoplasias, in cases ranging from relatively benign squamous metaplasias to cancerous invasive adenocarcinomas in which columnar epithelia are replaced by these tumors (Gray et al., 1999, Am. J. Pathol. 154:785-794; Zagouras et al., 1995, Proc. Natl. Acad. Sci. USA 92:6414-6418).

2.1.4 Notch Functions in Hematopoiesis

Evidence of Notch-1 mRNA expression in human CD34$^+$ precursors has led to speculation for a role for Notch signaling in hematopoiesis (Milner et al., 1994, Blood 3:2057-62). This is further supported by the recent demonstration that Notch-1 and -2 proteins are present in hematopoietic precursors and, in higher amounts, in T cells, B cells, and monocytes, and by the demonstration of Jagged-1 protein in hematopoietic stroma (Ohishi et al., 2000, Blood 95:2847-2854; Varnum-Finney et al., 1998, Blood 91:4084-91; Li et al., 1998, Immunity 8:43-55).

The clearest evidence for a physiologic role of Notch signaling has come from studies of T cell development which showed that activated Notch-1 inhibited B cell maturation but permitted T cell maturation (Pui et al., 1999, Immunity 11:299-308). In contrast, inactivation of Notch-1 or inhibition of Notch-mediated signaling by knocking out HES-1 inhibited T cell development but permitted B cell maturation (Radtke et al., 1999, Immunity 10: 47-58; Tomita et al., 1999, Genes Dev. 13:1203-10). These opposing effects of Notch-1 on B and T cell development raise the possibility that Notch-1 regulates fate decisions by a common lymphoid progenitor cell.

Other studies in transgenic mice have shown that activated Notch-1 affects the proportion of cells assuming a CD4 vs. CD8 phenotype as well as an αβ vs. γδ cell-fate (Robey et al., 1996, Cell 87:483-92; Washburn et al., 1997, Cell 88:833-43). Although this may reflect an effect on fate decisions by a common precursor, more recent studies have suggested that these effects may result from an anti-apoptotic effect of Notch-1 that enables the survival of differentiating T cells that would otherwise die (Deftos et al., 1998, Immunity 9:777-86; Jehn et al., 1999, J. Immunol. 162:635-8).

Evidence supporting a critical role for Notch signaling in myelopoiesis is less clear. In vivo studies involving overexpression or inactivation of Notch-1 have not identified significant effects of Notch-1 signaling on the development of mature myeloid elements, despite profound effects on T and B cell development (Pui et al., 1999, Immunity 11:299-308; Radtke et al., 1999, Immunity 10:547-58). However, in vitro studies have demonstrated effects of constitutively active Notch-1 forms on myelopoiesis. Constitutive overexpression of an activated form of Notch-1 inhibited G-CSF-induced granulocytic differentiation of murine 32D cells (Milner et al., 1996, Proc Natl Acad Sci U.S.A. 93:13014-9). More recent studies suggest that overexpression of the constitutively active intracellular domain of Notch-1 inhibits the differentiation of isolated murine hematopoietic precursors and enhances the generation of early precursor cells, including in vivo repopulating cells (Milner et al., 1996, Proc. Natl. Acad. Sci. U.S.A. 93:13014-13019; Bigas et al., 1998, J. Mol. Cell. Biol. 18:2324-2333). Thus, the lack of identifiable effects of Notch-1 on the in vivo generation of mature myeloid elements may result from compensatory effects due to other factors such as cytokines which may mask the effects of Notch activation in less mature precursors.

Studies have also shown that the differentiation of isolated hematopoietic precursor cells can be inhibited by ligand-induced Notch signaling. Coculture of murine marrow precursor cells (lin$^-$ Sca-1$^+$ c-kit$^+$) with 3T3 cells expressing human Jagged-1 led to a 2 to 3 fold increase in the formation of primitive precursor cell populations (Varnum-Finney et al., 1998, Blood 91:4084-4991; Jones et al., 1998, Blood 92:1505-11). Incubation of sorted precursors with beads coated with the purified extracellular domain of human Jagged-1 also led to enhanced generation of precursor cells (Varnum-Finney et al., 1998, Blood 91:4084-91).

In a study of human CD34$^+$ cells, expression of the intracellular domain of Notch-1 or exposure to cells that overexpressed Jagged-2 also led to enhanced generation of precursor cells and prolonged maintenance of CD34 expression (Carlesso et al., 1999, Blood 93:838-48). In another study, the effects of Jagged-1-expressing cells on CD34$^+$ cells were influenced by the cytokines present in the cultures; in the absence of added growth factors, the interaction with cell-bound Jagged-1 led to maintenance of CD34$^+$ cells in a non-proliferating, undifferentiated state, whereas the addition of c-kit ligand led to a 2-fold increase in erythroid colony-forming cells (Walker et al., 1999, Stem Cells 17:162-71).

Studies of more mature myeloid elements have also indicated a potential role for Notch signaling in regulating their cell-fate decisions. In those studies, immobilized, truncated Delta-1 inhibited the differentiation of CD14+monocytes into macrophages and induced apoptosis in the presence of specific cytokines (Ohishi et al., 2000, Blood 95:2847-2854; see Section 6). Further, ligand-induced Notch signaling is permissive for differentiation of monocytes into dendritic cells in the context of appropriate cytokine stimulation. Thus, as observed in other developing systems, Notch signaling appears to inhibit differentiation along a particular pathway, allowing cells to remain undifferentiated or to differentiate along the uninhibited, default pathway.

Notch signaling has been shown to play a central role in cell fate decisions in numerous developmental systems. The evolutionarily conserved Notch transmembrane receptors are known to play roles in differentiation, proliferation, and apoptotic events. In general, Notch signaling inhibits differentiation along a particular pathway, allowing the cell to remain undifferentiated or differentiate along an alternate pathway in response to specific environmental cues. Notch signaling is induced following receptor ligand interaction, causing proteolytic cleavage and release of an active intracellular domain which is transported to the nucleus and interacts with a number of downstream targets, including the transcriptional regulator, RBP-Jκ. At present, four paralogs of the Notch gene have been identified in vertebrates (Notch-1-4). The ligands for Notch are also transmembrane proteins and include Jagged-1 and -2, and Delta-1, -2, and -3. Evidence of expression of Notch-1 mRNA in human CD34+ precursors has led to speculation for a role for Notch signaling in hematopoiesis. Further studies have demonstrated Notch-1 and -2 protein in hematopoietic precursors and, in higher amounts, in T cells, B cells, and monocytes, as well as showing Jagged-1 to be expressed in hematopoietic stroma. The clearest evidence for a physiologic role of Notch signaling has come from studies of T cell development where Notch-1 mediated signaling is required for T cell development and affects CD4/CD8 and $\alpha\beta/\gamma\delta$ cell fate decisions, and constitutively active forms of Notch-1 induce T cell lymphomas. In addition, overexpression of a constitutively active Notch-1 form inhibits B cell maturation, suggesting that Notch-1 may regulate fate decisions by a common lymphoid progenitor cell. Evidence supporting a critical role for Notch signaling in myelopoiesis is less clear. Constitutive overexpression of an activated Notch-1 form inhibits G-CSF-induced granulocytic differentiation of 32D cells, and the differentiation of isolated hematopoietic precursors. The differentiation of precursor cells is also inhibited by ligand-induced Notch signaling. Coculture of murine marrow precursor cells (sca-1$^+$ lin$^-$ c-kit$^+$) with a 3T3 cell layer that expresses human Jagged-1 or incubating sorted precursors with beads coated with the purified extracellular domain of human Jagged-1 leads to a 2-3 fold increase in the formation of primitive precursor cell populations. Immobilized, truncated forms of the Notch ligand, Delta-1, were found to inhibit the differentiation of isolated precursors, allowing a substantial increase in the number of sca-1+lin$^-$ cells.

2.2 Cellular Differentiation During Development

The developmental processes that govern the ontogeny of multicellular organisms, including humans, depend on the interplay between signaling pathways, which gradually narrow the developmental potential of cells from the original totipotent stem cell to the terminally differentiated mature cell, which performs a specialized function, such as a heart cell or a nerve cell.

The fertilized egg is the cell from which all other cell lineages derive, i.e., the ultimate stem cell. As development proceeds, early embryonic cells respond to growth and differentiation signals which gradually narrow the cells' developmental potential, until the cells reach developmental maturity, i.e., are terminally differentiated. These terminally differentiated cells have specialized functions and characteristics, and represent the last step in a multi-step process of precursor cell differentiation into a particular cell.

The transition from one step to the next in cell differentiation is governed by specific biochemical mechanisms which gradually control the progression until maturity is reached. It is clear that the differentiation of tissues and cells is a gradual process which follows specific steps until a terminally differentiated state is reached.

Gastrulation, the morphogenic movement of the early embryonic cell mass, results in the formation of three distinct germ cell layers, the ectoderm, the mesoderm, and the endoderm. As cells in each germ cell layer respond to various developmental signals, specific organs are generated which are composed of specific differentiated cells. For example, the epidermis and the nervous system develop from ectoderm-derived cells, the respiratory system and the digestive tract are developed from endoderm-derived cells, and mesoderm-derived cells develop into the connective tissues, the hematopoietic system, the urogenital system, muscle, and parts of most internal organs.

The neural crest derives from the ectoderm and is the cell mass from which an extraordinary large and complex number of differentiated cell types are produced, including the peripheral nervous system, pigment cells, adrenal medulla and certain areas of the head cartilage.

The pluripotentiality of neural crest cells is well established (LeDouarin et al., 1975, Proc. Natl. Acad. Sci. USA 72:728-732). A single neural crest cell can differentiate into several different cell types.

The epidermis consists of several cellular layers which define a differentiation lineage starting from the undifferentiated, mitotically active basal cells to the terminally differentiated non-dividing keratinocytes.

The endoderm is the source of the tissues that line two tubes within the adult body. The digestive tube extends throughout the length of the body. The digestive tube gives rise not only to the digestive tract but also to, for example, the liver, the gallbladder and the pancreas. The second tube, the respiratory tube, forms the lungs and part of the pharynx. The pharynx gives rise to the tonsils, thyroid, thymus, and parathyroid glands.

The genesis of the mesoderm which has also been referred to as the mesengenic process gives rise to a very large number of internal tissues which cover all the organs between the ectodermal wall and the digestive and respiratory tubes.

Embryonic development produces the fully formed organism. The morphologic processes that define the cellular boundaries of each organ include not only proliferation and differentiation, but also apoptosis (programmed cell death). For example, in the nervous system, approximately 50% of neurons undergo programmed cell death during embryogenesis.

In the juvenile or adult individual, the maintenance of tissues, whether during normal life or in response to injury and disease, depends on the replenishing of the organs from precursor cells that are capable of responding to specific developmental signals.

The best known example of adult cell renewal via the differentiation of immature cells is the hematopoietic system. Here, developmentally immature precursors (hematopoietic stem and progenitor cells) respond to molecular signals to gradually form the varied blood and lymphoid cell types.

During hematopoietic development, the progeny of pluripotent stem cells progressively lose their proliferative potential and capacity for self-renewal, and display greater commitment to a given differentiation pathway. The factors that regulate this commitment to the various hematopoietic lineages are not understood, but are thought to include stochastic processes and interactions with soluble and cell-bound cytokines (Fairbairn et al., 1993, Cell 4:823-32; Ogawa, 1993, Blood 81:2844-53; Metcalf, 1989, Nature 339:27-30; Metcalf, 1993, Blood. 82:3515-23; Goldsmith et al., 1998, Proc. Natl. Acad. Sci. USA. 95:7006-11; Socolovsky et al., 1997, J. Biol. Chem. 272:14009-12).

While the hematopoietic system is the best understood self renewing adult cellular system it is believed that most, perhaps all, adult organs harbor precursor cells that under the right circumstances, can be triggered to replenish the adult tissue. For example, the pluripotentiality of neural crest cells has been described above. The adult gut contains immature precursors which replenish the differentiated tissue. Liver has the capacity to regenerate because it contains hepatic immature precursors; skin renews itself, etc. Through the mesengenic process, most mesodermal derivatives are continuously replenished by the differentiation of precursors. Such repair recapitulates the embryonic lineages and entails differentiation paths which involve pluripotent progenitor cells.

Mesenchymal progenitor cells are pluripotent cells that respond to specific signals and adopt specific lineages. For example, in response to bone morphogenic factors, mesenchymal progenitor cells adopt a bone forming lineage. For example, in response to injury, mesodermal progenitor cells can migrate to the appropriate site, multiply and react to local differentiation factors, consequently adopting a distinct differentiation path.

It has been suggested that the reason that only a limited tissue repair is observed in adults is because there are too few progenitor cells which can adopt specific differentiation lineages. It is clear that if these cells can be expanded by immortalizing them in culture, then tissue repair could be facilitated by transplantation of the cultured cells. However, diploid cells generally have a limited proliferative capacity in vitro. Following initial culturing, the cells undergo a series of rapid cycling, which slows down until the population undergoes a growth arrest, which is a result of a block at the G1/S or G2/M phases of mitosis (Derventz et al., 1996, Anticancer Res. 16:2901-2910). For example, after a limited number of divisions, human fibroblasts enter a nonreplicative state as a result of cellular senescence. When certain viral oncogenes are expressed in the fibroblasts, the replicative life span is extended, but the cells still enter a nonreplicative state termed a "crisis" state (Wei and Sedivy, 1999, Exp Cell Res 253:519-522). The number of cell cycles a cell undergoes before reaching the growth arrest phase depends on the cell type; for human cells, the number is generally between 30 and 60 (Derventz et al., 1996, Anticancer Res. 16:2901-2910 and reference cited therein). Therefore, the process of immortalizing pluripotent or multipotent cells, such as stem or progenitor cells of a desired type, ex vivo would give rise to more rapid proliferation of the desired cell type and allow for more rapid treatment injuries or traumas. Additionally, the ability would give rise to the potential for treating many human diseases, would circumvent tissue rejection without the need for immunosuppressive agents.

Citation or identification of any reference in Section 2 or any other section of this application shall not be construed as an admission that such reference is available as prior art to the present invention.

3 SUMMARY OF THE INVENTION

The present invention provides methods for producing immortalized precursor cell populations comprising culturing non-immortalized precursor cells in the presence of a Notch agonist and one or more growth factors, for a time period beyond which cells of said precursor cell type not in the presence of said Notch agonist and said growth factors stop proliferating and/or die, such that said precursor cell proliferates but does not terminally differentiate during said time period, thereby producing an immortalized precursor cell population. In a preferred embodiment, the precursor cell population does not substantially differentiate during said time period. As used herein, the phrase "the precursor cell population does not substantially differentiate" indicates that the majority of the cells in the precursor cell population do not different. In one embodiment, at least 60% of the cells in the precursor cell population do not differentiate. In other embodiments, at least 65%, more preferably at least 70%, and yet more preferably at least 75% of the cells in the precursor cell population do not differentiate. In yet other embodiments, at least 80%, 85%, 90%, 95% or 99% of the cells in the precursor cell population do not differentiate.

In one embodiment, the precursor cell is a stem cell. In one mode of the embodiment, the stem cell is a hematopoietic stem cell (HSC). In another embodiment, the precursor cell is a progenitor cell. In one mode of the embodiment, the progenitor cell is a hematopoietic progenitor cell. A hematopoietic stem or progenitor cell can obtained from bone marrow, fetal blood or neonatal blood.

Wherein the precursor cell is an HSC, the time period for which the precursor cells are cultured in the presence of a Notch agonist and one or more growth factors is preferably four weeks. In another embodiment, the time period is five weeks. In yet another embodiment, the time period is six weeks.

Wherein the precursor cell is an HSC, the growth factor in whose presence the precursor cell is cultured according to one embodiment of the invention is stem cell factor (SCF). Preferably, said culturing step is in culture medium containing SCF at a concentration of 100 ng/ml. In another embodiment, the growth factors are SCF, interleukin-6 (IL-6), interleukin-11 (IL-11) and Flt-3 ligand (Flt-3L). In a preferred mode of the embodiment, said culturing step is in culture medium containing SCF, IL-6 and Flt-3L at a concentration of 100 ng/ml each and IL-11 at a concentration of 10 ng/ml.

In one embodiment of the present invention, the immortalized precursor cell population is a clonal cell population. Limited dilution cloning can be used to isolate a clonal cell line.

In a preferred embodiment, the precursor cell of the invention is a human cell. In another embodiment, the precursor cell is a murine cell, most preferably a murine marrow hematopoietic precursor cell that is lin− Sca-1+c-kit+.

A Notch agonist can be a deletion form of a Notch protein consisting essentially of the intracellular domain of the Notch protein expressed recombinantly in the precursor cell. In certain specific embodiments, Notch protein is selected from the group consisting of human and murine Notch-1, Notch-2, Notch-3 and Notch-4. A Notch antagonist can alternatively be a Delta protein. In a preferred embodiment, the Delta protein is Delta$^{ext-IgG}$.

The present invention further provides methods for producing differentiated cells comprising culturing non-immortalized precursor cells in the presence of a Notch agonist, a first one or more growth factors that promote proliferation but not differentiation of said precursor cell and a second one or more growth factors that promote differentiation of said precursor cell, for a time period beyond which cells of said precursor cell type not in the presence of said Notch agonist and said first growth factors stop proliferating and/or die, such that said precursor cell proliferates and differentiates during said time period, thereby producing a differentiated cell population. Alternatively, the methods for producing differentiated cells comprise producing an immortalized precursor cell population according to the methods disclosed herein, wherein said precursor cell is a primary HSC, and exposing one or more cells of said immortalized precursor cell population to an effective amount of one or more differentiation-promoting growth factors under conditions conducive to differentiation.

The present invention further provides a composition comprising a cell, such as an HSC, in culture in contact with a Delta protein comprising a Notch-interacting domain, wherein said Delta protein has been immobilized on the surface of the culture receptacle, such as a plastic plate, well or bottle. In one embodiment, the cell in culture is further in contact with an extracellular matrix protein such a fibronectin which is also coated or bound onto the surface of the cell culture receptacle. The Delta protein is preferably epitope tagged so that it can be immobilized onto the surface of the cell culture receptacle through an antibody or other protein that binds to the epitope tag.

The present invention further provides methods for treating a subject in need of cell therapy comprising producing an immortalized precursor cell population according to the methods disclosed herein and administering one or more immortalized precursor cells from said immortalized precursor cell population to the subject. Alternatively, a method for treating a subject in need of cell therapy comprises producing differentiated cells according to the methods described herein, and administering one or more of said differentiated cells to the subject.

The present invention further provides methods for producing a lymphoid stem cell, said method comprising producing an immortalized precursor cell population according to the methods described herein, wherein said precursor cell is a primary HSC, and exposing an immortalized HSC from said immortalized precursor cell population to SCF and interleukin-7 (IL-7) in amounts effective to cause differentiation of said HSC to produce a lymphoid stem cell.

The present invention further provides methods for treating a subject in need of lymphoid stem cell therapy, comprising producing a lymphoid stem cell according to the methods disclosed herein and administering one or more of the lymphoid stem cells to the subject.

The present invention further provides methods for producing a myeloid stem cell, said method comprising producing an immortalized precursor cell population according to the methods disclosed herein, wherein said precursor cell is a primary HSC, and exposing an immortalized HSC from said immortalized precursor cell population to SCF and GM-colony stimulating factor (GM-CSF) in amounts effective to cause differentiation of said HSC to produce a myeloid stem cell.

The present invention further provides methods for treating a subject in need of myeloid stem cell therapy, comprising producing a myeloid stem cell according to the methods disclosed herein, and administering one or more of said myeloid stem cell to the subject.

The present invention further provides methods for producing a high proliferative potential colony forming cell (HPP-CFC), said method comprising producing an immortalized precursor cell population according to the methods disclosed herein, wherein said precursor cell is a primary HSC, and exposing an immortalized HSC from said immortalized precursor cell population to a Notch agonist and an amount of a retinoic acid receptor (RAR) ligand in an amount effective to cause differentiation of said HSC to produce a HPP-CFC. In a preferred embodiment, the RAR ligand is all-trans retinoic acid (ATRA).

The present invention further provides methods for treating a subject in need of HPP-CFC therapy, comprising producing an HPP-CFC according to the methods disclosed herein, and administering one or more HPP-CFCs to the subject.

The present invention further provides a clonal hematopoietic cell culture comprising a population of hematopoietic precursor cells exposed for at least four weeks to a Notch agonist and SCF, IL-6, IL-11 and Flt-3L in amounts effective to promote proliferation of said precursor cells, but substantially not differentiation. In a preferred embodiment, the hematopoietic precursor cells are stem cells. In another preferred embodiment, the hematopoietic precursor cells are sca-+lin− c-kit+murine cells constitutively expressing an activated Notch mutant protein. The present invention further provides an isolated hematopoietic precursor cell line that constitutively overexpresses an activated Notch protein. In a specific embodiment, the cells are transformed with a nucleic acid comprising, in a 5' to 3' order, a constitutively active promoter, and the following sequences operably linked to said promoter: a first open reading frame encoding a mutant Notch-1 protein consisting essentially of the cytoplasmic domain of the Notch-1 protein, an internal ribosomal entry site, and a second open reading frame encoding green fluorescent protein.

The present invention yet further provides methods for screening for a Notch agonist, comprising culturing a non-immortalized precursor cell in the presence of a test molecule and one or more growth factors for a time period beyond which cells of said precursor cell type not in the presence of a Notch agonist and said growth factors stop proliferating and/or die, and detecting whether or not said cells proliferate without terminally differentiating, wherein the ability of the precursor cell or its progeny to proliferate but not terminally differentiate during said time period is indicative that the test molecule is a Notch agonist.

The present invention yet further provides methods for screening for a growth factor that promotes proliferation but not differentiation of a precursor cell, comprising culturing a non-immortalized precursor cell in the presence of a test molecule and a Notch agonist for a time period beyond which cells of said precursor cell type not in the presence of said Notch agonist and one or more growth factors that promote proliferation but not differentiation of said precursor cell stop proliferating and/or die, and detecting whether or not said cells proliferate without terminally differentiating, wherein the ability of the precursor cell or its progeny to proliferate but not terminally differentiate during said time period is indicative that the test molecule is a growth factor that promotes proliferation but not differentiation of the precursor cell.

The present invention yet further provides methods for screening for a Notch antagonist, comprising culturing a non-immortalized precursor cell in the presence of a test molecule, a Notch agonist and one or more growth factors for a time period beyond which cells of said precursor cell type not in the presence of said Notch agonist and said growth factors stop proliferating and/or die, and detecting whether or not said cells proliferate without terminally differentiating, wherein the failure of the precursor cell or its progeny to proliferate without terminally differentiating during said time period, which failure is rescued by the addition of a higher amount of Notch agonist, is indicative that the test molecule is a Notch antagonist.

The present invention yet further provides methods for identifying a gene differentially expressed between a precursor cell type and a more differentiated cell type, comprising culturing a non-immortalized precursor cell in the presence of a Notch and one or more growth factors that promote proliferation but not differentiation of said precursor cell and a second one or more growth factors that promote differentiation of said precursor cell, for a time period beyond which cells of said precursor cell type not in the presence of said Notch agonist and said growth factors stop proliferating and/or die, exposing one or more cells of said immortalized precursor cell population to an effective amount of one or more differentiation-promoting growth factors under conditions conducive to differentiation, thereby producing a more differentiated cell population, and comparing the gene expression profile of the precursor cell or its progeny to the gene expression profile of the more differentiated cell type, wherein a gene whose level of expression differs between the precursor cell and the more differentiated cell is said to be differentially expressed between the precursor cell type and the more differentiated cell type. In one embodiment, the gene or gene product is characterized by increased gene expression in the more differentiated cell. In another embodiment, the gene or gene product is characterized by reduced gene expression in the more differentiated cell. In a specific embodiment, the gene expression profile of each cell is assayed by detecting the presence or measuring the amount of individual proteins present in the cell. In another specific embodiment, the gene expression profile of each cell is assayed by detecting the presence or measuring the amount of individual mRNAs present in the cell.

The present invention yet further provides a kit comprising in one or more containers one or more purified growth factors that promote proliferation but not differentiation of a precursor cell and a purified Notch agonist, which growth factors and Notch agonist are together effective to immortalize a precursor cell exposed to them in culture. Optionally, the kit further comprises in a separate container one or more purified growth factors that promote the differentiation of the precursor cell.

3.1 Abbreviations and Definitions

As used herein, the following abbreviations and definitions will have the meanings indicated:

ATRA: all trans retinoic acid.
BDNF: Brain-derived neurotrophic factor
BFU-E: burst-forming unit-erythroid. An hematopoietic progenitor cell which is capable of producing a colony of erythroid progeny cells in semi-solid medium.
CFU or CFU-C: colony-forming unit or colony-forming unit cell. A cell which is capable of producing a colony of progeny cells in semi-solid medium.
CFU-E/Mega: colony-forming unit-erythrocyte, megakaryocyte. An hematopoietic progenitor cell which is capable of producing a colony composed of erythrocyte and megakaryocyte progeny in semi-solid medium.
CFU-Eo: colony-forming unit-eosinophil. An hematopoietic progenitor cell which is capable of producing a colony composed of eosinophil progeny in semi-solid medium.
CFU-G: colony-forming unit-granulocyte. An hematopoietic progenitor cell which is capable of producing a colony composed of granulocyte (or polymorphonuclear leukocyte) progeny in semi-solid medium.
CFU-GM: colony-forming unit-granulocyte, macrophage. An hematopoietic progenitor cell which is capable of producing a colony composed of granulocyte and macrophage progeny in semi-solid medium.
CFU-M: colony-forming unit-macrophage. An hematopoietic progenitor cell which is capable of producing a colony composed of macrophage progeny in semi-solid medium.
CFU-Mega: colony-forming unit-megakaryocyte. An hematopoietic progenitor cell which is capable of producing a colony composed of megakaryocyte progeny in semi-solid medium. Megakaryocytes are the precursors of platelets.
CFU-S: colony forming unit-spleen. A multipotential stem cell with self-renewal capacity, which, upon inoculation into lethally-irradiated mice, is capable of producing a colony (nodule) on the spleen(s) containing megakaryocyte, granulocyte and erythroid precursors.
CNTF: Ciliary neurotrophic factor
EGF: Epidermal growth factor
EPO: Erythropoietin
FGF-1: Fibroblast growth factor-1/acidic FGF
FGF-2: Fibroblast growth factor-2/basic FGF
FGF-7: Fibroblast growth factor-7
Flt-3L: flt-3 ligand
GDNF: glial cell line-derived neurotrophic factor
GM-CSF: granulocyte-macrophage colony stimulating factor
HGF: Hepatocyte growth factor
HSC: hematopoietic stem cell. The definition of an HSC is functional and based upon the ability of transplanted cells to repopulate the hematopoietic system of a recipient who has undergone myeloablative treatment. HSCs represent approximately 0.01% of bone marrow cells. They can self-renew and can be assayed by their ability to regenerate the bone marrow and to give rise to long-term lympho- and myelopoiesis (Dexter and Allen, 1992, Nature 360:709-710).
HPP-CFC or HPP-mix: high proliferative potential colony forming cell, which is an immature myeloid stem cell.
IGF-1: Insulin-like growth factor-1
IL-3: interleukin-3
IL-6: interleukin-6
IL-7: interleukin-7
IL-11: interleukin-11
IRES: internal ribosomal entry site
Lymphoid stem cell: A lymphoid stem cell has limited self renewal capacity and is capable of regenerating entire lymphoid lineages and of producing a colony composed of all lymphoid cell types (see FIG. 1) in semi-solid medium. Murine lymphoid stem cells are marked by their expression of CD25.
Myeloid stem cell: A myeloid stem cell has limited self renewal capacity and is capable of regenerating entire myeloid lineages and of producing a colony composed of all myeloid cell types (see FIG. 1) in semi-solid medium. Murine myeloid stem cells are identified by the expression of Gr-1 and F4/80.
NGF: Nerve growth factor
PDGF: Platelet-derived growth factor
RAM: RBPJκ binding domain of Notch
RAR: retinoic acid receptor
SCF: stem cell factor, also known as the c-kit ligand or mast cell growth factor
TGF-β: transforming growth factor-β
Tpo: thrombopoietin

4 BRIEF DESCRIPTION OF THE FIGURES

FIG. 1. Schematic diagram of hematopoietic stem cell (HSC) differentiation. Reproduced from p. 827 of Cecil Textbook of Medicine, Sixteenth Edition (1982), Wyngaarden and Smith, Eds., W.B. Saunders Company. The differentiation potential of hematopoietic cells is described in U.S. Pat. No.

5,612,211 to Wilson and Gabrilove. Lymphoid and myeloid stem cells are also commonly referred to in the art as lymphoid and myeloid progenitor cells.

Figure 2:
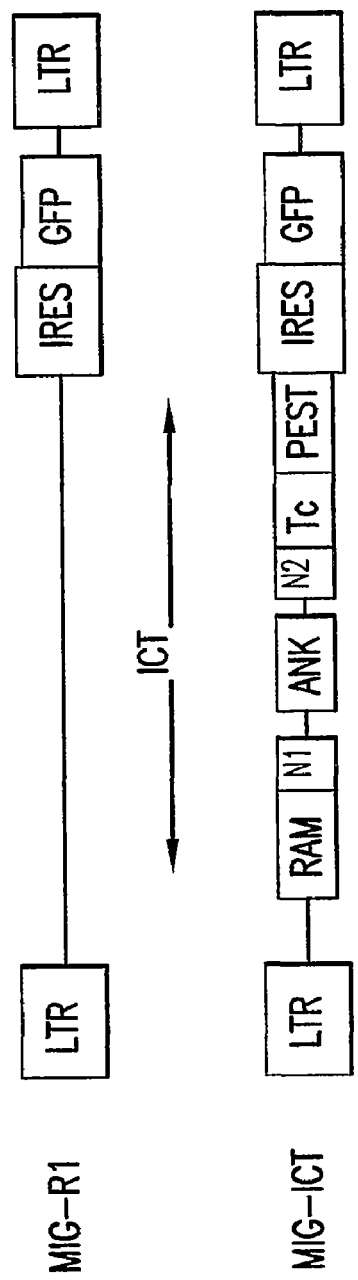

FIG. 2. Schematic diagram of retroviral constructs used to transduce murine lin$^-$ Sca-1+c-kit$^+$ murine marrow cells. An MSCV-based retrovirus with an internal ribosomal entry site (IRES) and GFP encoding sequences. ICT encodes the intracellular domain of murine Notch-1 and consists of RBPJκ binding domain (RAM), nuclear localization domains (N1, N2), ankyrin repeats (ANK), and the C-terminal transactivation domain (Tc).

Figures 3A, 3B:
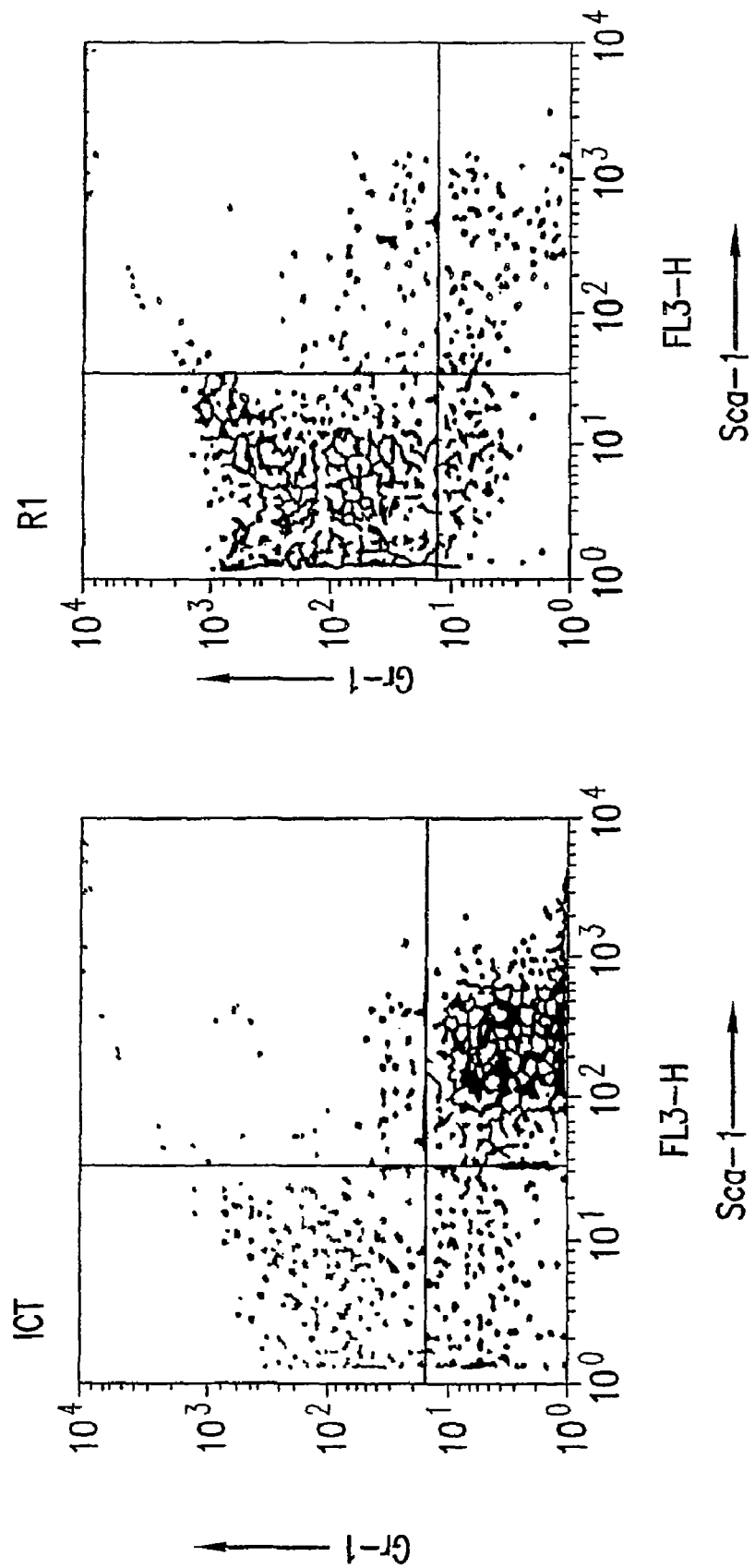

FIG. 3. Notch activation maintains Sca-1$^+$-Gr-1$^-$ cell type. Cells expressing activated Notch (ICT) or control virus (R1) were cultured for a total of 12 days and then stained with antibodies to Sca-1 and Gr-1. Dot plots represent fluorescence intensity for Sca-1 on the x-axis and for Gr-1 on the y-axis.

Figure 4A:
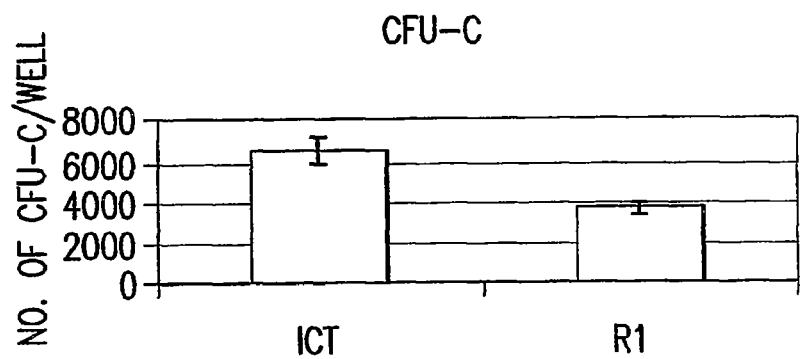
Figure 4B:
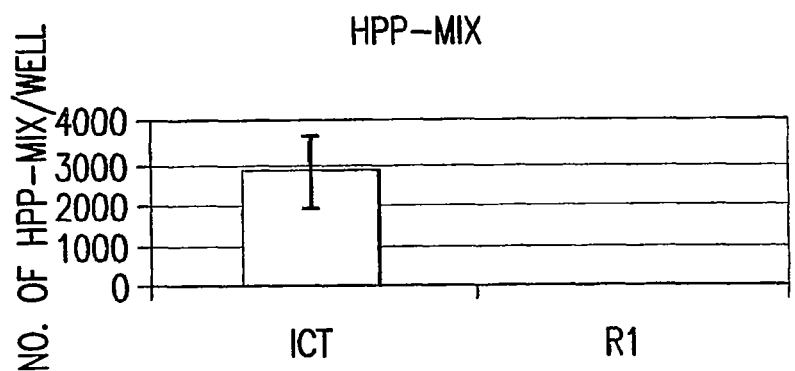
Figure 5A:
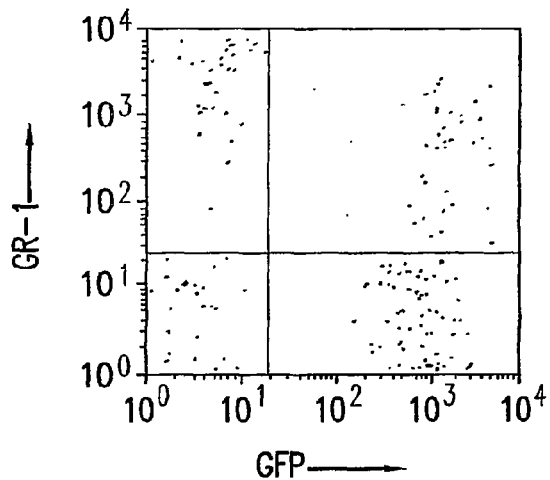
Figure 5B:
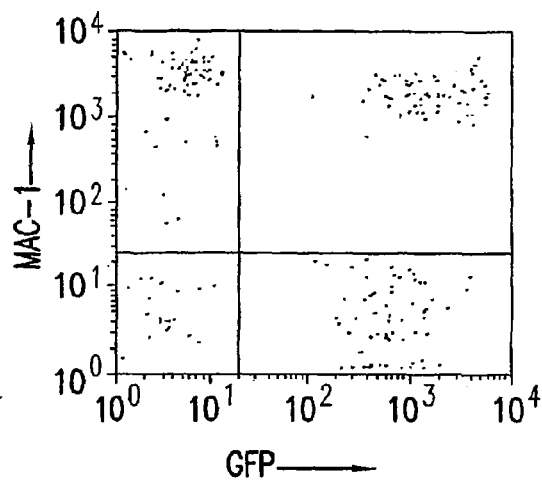
Figure 5C:
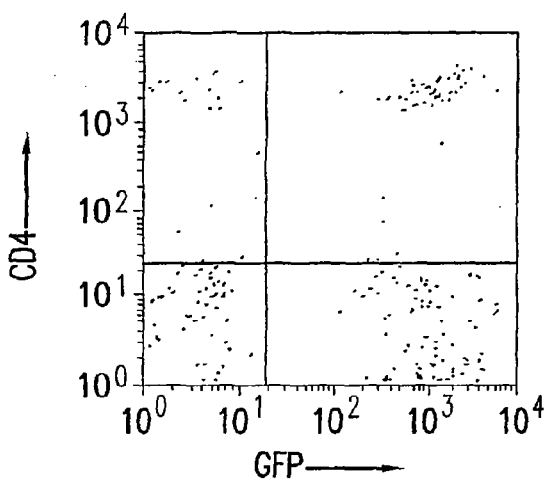
Figure 5D:
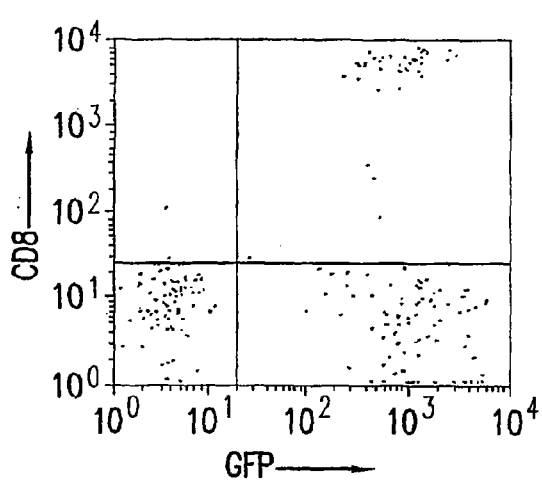

FIG. 4. Notch activation immortalizes precursor cell types HPP-mix and CFU-C. Cells expressing activated Notch (ICT) or control virus (R1) were cultured for 12 days and replated in semisolid medium. After 10 days colonies were identified and counted. HPP-mix generate colonies with a diameter greater than 1.5 mm that consist of granulocytes, macrophages and erythroid clusters. CFU-C generate colonies of any type consisting of more than 50 cells.

FIG. 5. Short-term repopulating ability of activating Notch-1-expressing precursor cells. Dot plots represent fluorescence intensity for GR-1, Mac-1, CD4, CD8 on the y-axis and GFP on the x-axis.

FIG. 6. Ligand-induced Notch activation maintains Sca-1$^+$, Gr-1$^-$ cell type. Cells incubated with immobilized Delta$^{ext-IgG}$ or control$^{IgG}$ for a total of 13 days were stained with antibodies to Sca-1 and Gr-1. Dot plots represent fluorescence intensity for Sca-1 on the x-axis and for Gr-1 on the y-axis.

Figure 7A:
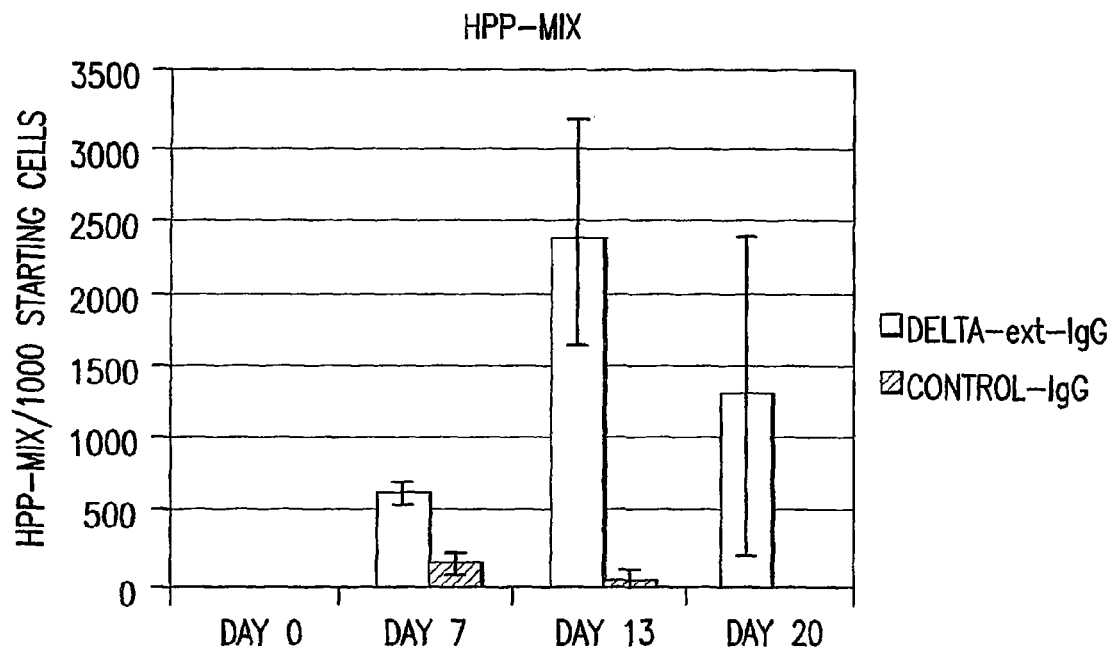
Figure 7B:
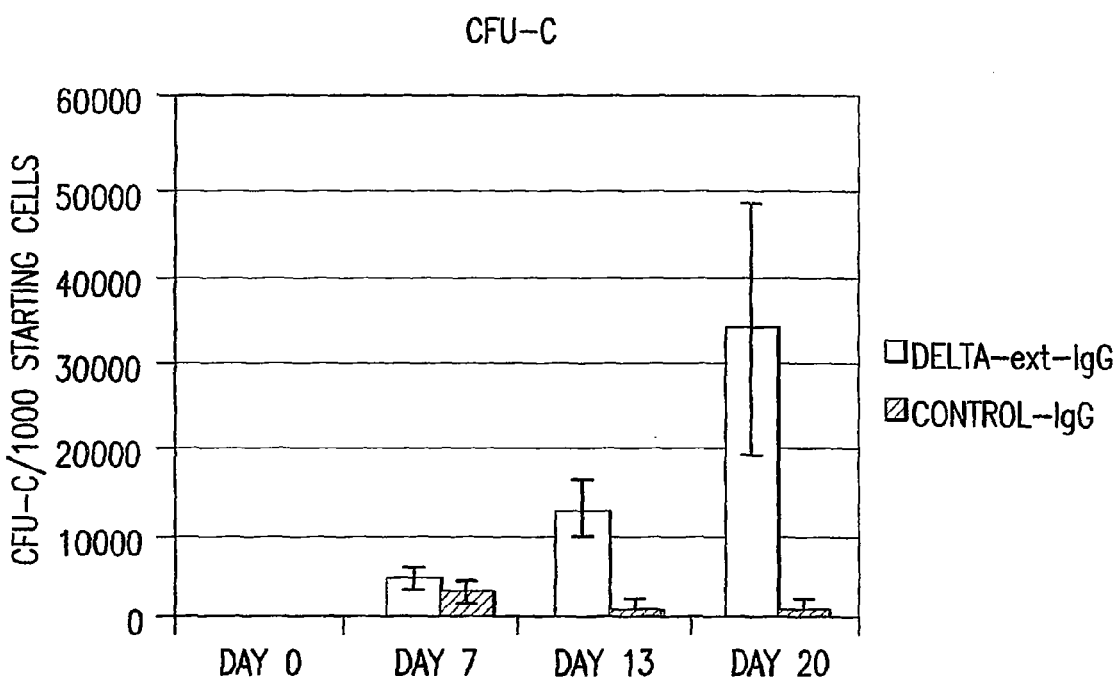

FIG. 7. Ligand-induced Notch activation immortalizes precursor cell types CFU-C and HPP-mix. Cells were incubated with immobilized Delta$^{ext-IgG}$ or control$^{IgG}$ for a total of 7, 13 or 20 days and re-plated in semisolid medium. After 10 days, colonies were identified and counted. HPP-mix generate colonies with a diameter greater than 1.5 mm that consist of granulocytes, macrophages, and erythroid, clusters. CFU-C generate colonies of any type consisting of more than 50 cells.

Figure 8:
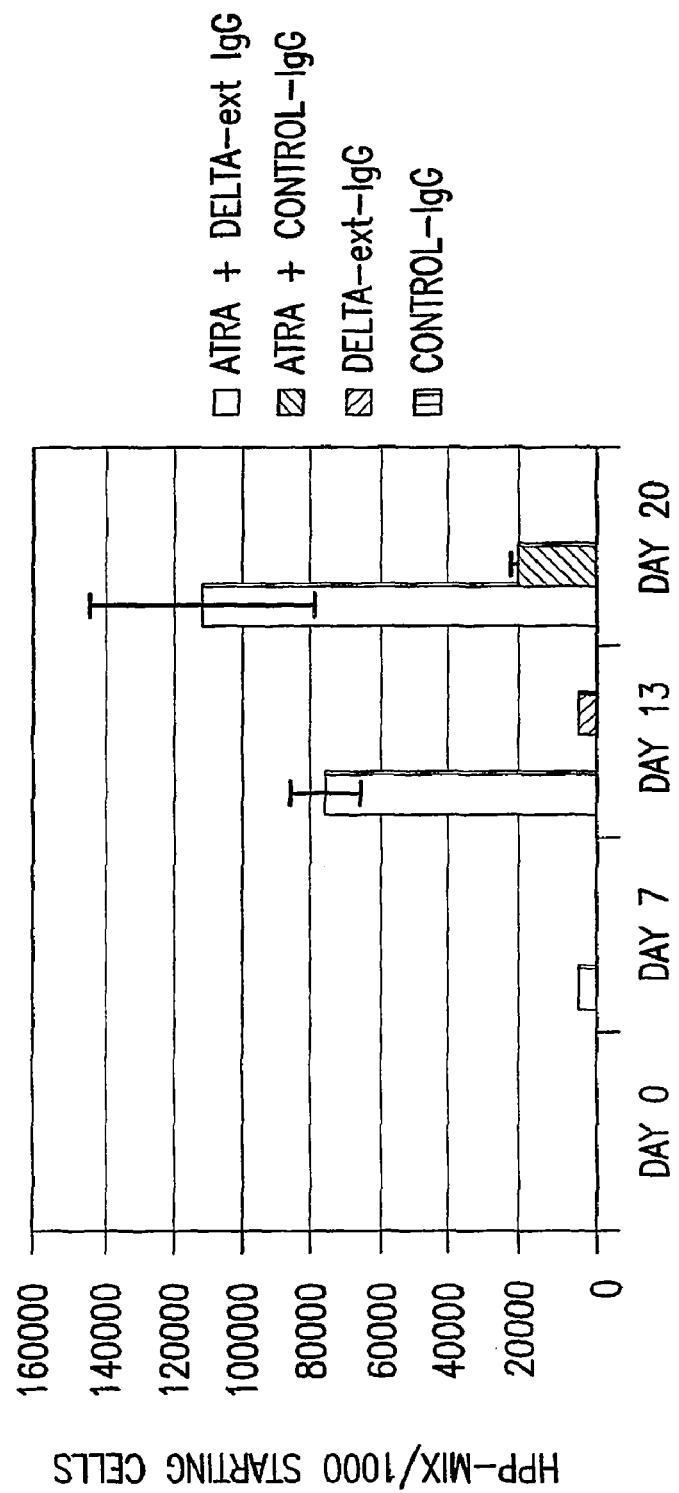

FIG. 8. ATRA and ligand-induced Notch activation synergizes to immortalize precursor cell type HPP-mix. Cells were incubated with immobilized Delta$^{ext-IgG}$ or control$^{IgG}$ with or without ATRA for 7, 13, or 20 days and replated in semisolid medium. After 10 days colonies were identified and counted.

Figure 9:
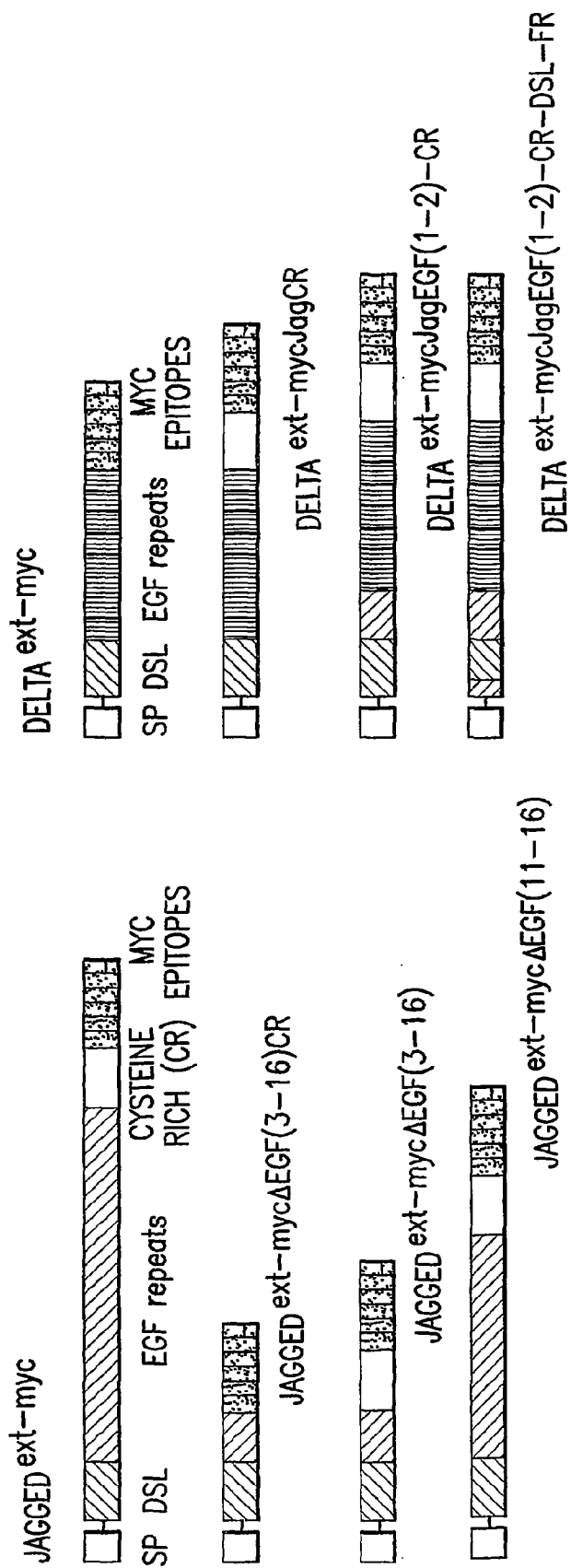

FIG. 9. Schematic diagrams are presented of soluble fusion proteins comprising the extracellular domain of Jagged and Delta and either the Fc domain of an immunoglobulin or myc epitopes.

5 DETAILED DESCRIPTION OF THE INVENTION

The present invention provides methods for producing immortalized cell populations of non-terminally differentiated cells. Cells immortalized by the methods of the present invention are hereinafter referred to as Immortalized cells. In particular, the present invention provides methods of growing precursor cells (non-terminally differentiated cells) in culture for a period beyond which the cells would otherwise stop proliferating and/or die, due to senescence and/or undergoing crisis leading to cell death. The methods comprise exposing the cell to an agonist of the Notch pathway and one or more growth factors that promotes proliferation but not differentiation of the precursor cells.

The present invention further provides methods for producing a desired differentiated cell type from less differentiated types, comprising immortalizing a precursor cell according to the methods of the invention and then exposing the Immortalized cell and/or its progeny to conditions that promote differentiation of the precursor cell into the desired cell type. A cell differentiated by the methods of the present invention is hereinafter referred to as a Differentiated cell.

These methods can be used to produce cells for repopulation or replenishment of a depleted cell population, for example reconstitution of hematopoietic cells following chemotherapy or T-cells following infection with the Human Immunodeficiency Virus. The cells Immortalized or Differentiated by the methods of the present invention can also be made recombinant, for example to deliver a desired gene product. These methods can also be used as a basis for screening for Notch pathway agonists and antagonists, and for screening for genes that are preferentially expressed in one cell type over another cell type, for example by identifying genes that are not expressed in a precursor cell type but whose expression is induced upon exposure to differentiation cues, or vice versa. Clonal cell lines can be made from the Immortalized cells, for example, by limited dilution cloning.

In certain embodiments of the present invention, Immortalized cells are transplanted back into the appropriate region of a subject's body, for example Immortalized HSCs into the subject's bone marrow. In another embodiment, the Immortalized cells are differentiated by activation of the Notch pathway and/or by altering the combination of growth factors in which the cells are grown, according to the methods of the present invention or by any method known in the art. In yet another embodiment, the precursor stem cells are concurrently immortalized and differentiated by a combination of Notch pathway activation and appropriate growth factors (for example as described in Section 6.4, infra) then transplanted back into the subject. Preferably, the Notch pathway agonist is inactivated prior to transplantation into a subject.

The present invention further provides cultures and HSCs produced by the methods described herein.

The present invention yet further provides kits comprising reagents for immortalizing or immortalizing and differentiating cells, including but not limited to a Notch agonist and a growth factor which together are capable of immortalizing a precursor cell exposed to them.

5.1 Notch Agonists

The methods of the present invention encompass immortalizing precursor cells (non-terminally differentiated cells) in the presence of a Notch agonist and one or more growth factors for a given period of time. A Notch agonist is an agent that promotes, i.e., causes or increases, activation of Notch pathway function. As used herein, "Notch pathway function" shall mean a function mediated by the Notch signaling pathway, including but not limited to nuclear translocation of RBP-Jκ or its *Drosophila* homolog Suppressor of Hairless; activation of bHLH genes of the Enchancer of split complex, e.g. Mastermind; inhibition of *Drosophila* neuroblast segregation; and binding of Notch to Delta, Jagged/Serrate, Fringe, Deltex or RBP-Jκ/Suppressor of Hairless, or homologs or analogs thereof.

Notch activation is carried out by exposing a precursor cell to a Notch agonist. The agonist of Notch can be but is not limited to a soluble molecule, recombinantly expressed as a cell-surface molecule, on a cell monolayer to which the precursor cells are exposed, or a molecule immobilized on a solid phase. In a preferred mode of the embodiment, the Notch agonist is immobilized Delta$^{ext-myc}$ or Delta$^{ext-IgG}$. In another embodiment, the Notch agonist can be recombinantly expressed from a nucleic acid introduced into the precursor cells. Notch agonists of the present invention include but are not limited to Notch proteins and analogs and derivatives (including fragments) thereof, proteins that are other elements of the Notch pathway and analogs and derivatives (including fragments) thereof, antibodies thereto and fragments or other derivatives of such antibodies containing the binding region thereof, nucleic acids encoding the proteins and derivatives or analogs; as well as toporythmic proteins and derivatives and analogs thereof which bind to or otherwise interact with Notch proteins or other proteins in the Notch pathway such that Notch pathway activity is promoted. Such agonists include but are not limited to Notch proteins and derivatives thereof comprising the intracellular domain, Notch nucleic acids encoding the foregoing, and proteins comprising the Notch-interacting domain of Notch ligands (e.g., the extracellular domain of Delta, Jagged, Serrate). Other agonists include but are not limited to RBPJκ/Suppressor of Hairless or Deltex. Fringe can be used to enhance Notch activity, for example in conjunction with Delta proteins. These proteins, fragments and derivatives thereof can be recombinantly expressed and isolated or can be chemically synthesized. Wherein the Notch agonist is expressed in the precursor cell itself, for example a dominant active form of Notch, via a recombinant nucleic acid, identification of cells expressing the Notch agonist can be facilitated by the introduction of an internal ribosome entry site (IRES) followed by an open reading frame encoding a marker protein 3' to the open reading frame of the Notch agonist in the recombinant nucleic acid construct. Preferably, a marker protein is a fluorescent protein such as green fluorescent protein (GFP; see e.g., U.S. Pat. Nos. 5,491,084 and 5,777,079); GFP modified to fluoresce at a different intensity and/or wavelength (e.g. blue GFPs, as described by Heim and Tsien, 1996, Curr. Biol. 6:178-82) or the yellow or red-orange emitter recently discovered in reef corals (Matz et al., 1999, Nature Biotechnol. 17:969-973).

In another specific embodiment, the Notch agonist is a cell which expresses a protein or fragment or derivative thereof, which agonizes Notch. The cell expresses the Notch agonist in such a manner that it is made available to the precursor cells, e.g., secreted, expressed on the cell surface, etc. In yet another specific embodiment, the Notch agonist is a nucleic acid that encodes a protein or fragment or derivative thereof which agonizes Notch; such an agonist can, for example, be employed or delivered according to the methods described in Section 5.3, infra.

In yet another specific embodiment, the agonist of Notch is a peptidomimetic or peptide analog or organic molecule that binds to a member of the Notch signaling pathway. Such an agonist can be identified by binding assays selected from those known in the art.

In a preferred embodiment the agonist is a protein consisting of at least a fragment of a protein encoded by a Notch-interacting gene which mediate binding to Notch proteins or adhesive fragments thereof. Notch interacting genes, as used herein, shall mean the genes Notch, Delta, Jagged, Serrate, RBPJκ, Suppressor of Hairless and Deltex, as well as other members of the Delta/Serrate/Jagged family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g. in Drosophila). Adhesive fragments of Notch-binding proteins cited above are described in U.S. Pat. Nos. 5,648,464; 5,849, 869; and 5,856,441).

In one embodiment, the Notch agonist is expressed from a recombinant nucleic acid. For example, expression of truncated, "activated" forms of the Notch receptor lacking the extracellular, ligand binding domain results in gain of function mutant phenotypes. Preferably, the Notch dominant active mutant is expressed by the precursor cells from an inducible promoter, such that expression can be induced for expansion and/or differentiation, with the inducer lacking in vivo in the organism from which the cells are from so that the transplanted cells can respond to their environmental cues. In another embodiment, the nucleic acid encoding the Notch agonist is flanked by Cre sites. Following expansion and/or differentiation of the precursor cell but prior to transplantation to a subject, the progeny cells comprising the nucleic acid are exposed to Lox protein, as described in Section 5.12 below. Alternatively, the FLP/FRT recombination system can be used to control the presence and expression of a Notch agonist (Brand and Perrimon, 1993, Development 118:401-415).

Alternatively, in another embodiment the agonist of Notch is not a recombinant dominant Notch active mutant.

Alternatively, in another embodiment, exposure of the precursor cells to a Notch agonist is not done by incubation with other cells recombinantly expressing a Notch ligand on the cell surface (although in other embodiments, this method can be used).

In another embodiment, the recombinantly expressed Notch agonist is a chimeric Notch protein which comprises the intracellular domain of Notch and the extracellular domain of another ligand-binding surface receptor. For example, a chimeric Notch protein comprising the EGF receptor extracellular domain and the Notch intracellular domain is expressed in a precursor cell. However, the Notch pathway will not be active unless the precursor cell expressing the chimera is exposed to the ligand of the EGF receptor, i.e., EGF. As with the inducible promoter controlling the expression of the truncated form of Notch, the activity of the chimeric Notch protein is reversible; when EGF is removed from the cells, Notch activity will cease. Notch activity can again be turned on with the addition of the ligand. Preferably, the chimeric receptor is expressed under the control of an inducible promoter which is turned off, for example by removing the inducer, prior to transplantation of the Immortalized cells, so that the transplanted cells do not respond to EGF in vivo by the activation of the Notch pathway.

In yet other embodiments, Notch activity can be manipulated by the binding of Notch ligands (e.g., Delta, Jagged/Serrate) to the extracellular portion of the Notch receptor. Notch signaling appears to be triggered by the physical interaction between the extracellular domains of Notch and its ligands that are either membrane-bound on adjacent cells or immobilized on a solid surface. Full length ligands are agonists of Notch, as their expression on one cell triggers the activation of the pathway in the neighboring cell which expresses the Notch receptor. Soluble truncated Delta or Serrate molecules, comprising extracellular domains of the proteins or Notch-binding portions thereof, that have been immobilized on a solid surface, such as a tissue culture plate, are particularly preferred Notch pathway agonists. Such soluble proteins can be immobilized on a solid surface by an antibody or interacting protein, for example an antibody directed to an epitope tag with which Delta or Serrate is expressed as a fusion proteins (e.g., a myc epitope tag, which is recognized by the antibody 9E10) or a protein which interacts with an epitope tag with which Delta or Serrate is expressed as a fusion protein (e.g., an immunoglobulin epitope tag, which is bound by Protein A). Soluble truncated Delta or Serrate molecules which lack intracellular domains act as antagonists of the pathway, as their expression results in non-autonomous, dominant negative phenotypes in neighboring Notch-expressing cells.

In another specific embodiment, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the furin-like convertase required for Notch processing, Kuzbanian, the metalloprotease-disintegrin (ADAM) thought to be required for the activation of the Notch pathway upstream or parallel to Notch (Schlondorff and Blobel, 1999, J. Cell Sci. 112:3603-3617), or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a furin, Kuzbanian or rab protein, or a fragment or derivative or dominant active mutant thereof, or a peptidomimetic or peptide analog or organic molecule that binds to and activates the function of the above proteins. The peptidomimetic or peptide analog or organic molecule can be identified by the assays described above.

Finally, U.S. Pat. No. 5,780,300 further discloses classes of Notch agonist molecules (and methods of their identification) which can be used to activate the Notch pathway in the practice of the present invention, for example molecules that trigger the dissociation of the Notch ankyrin repeats with RBP-Jκ, thereby promoting the translocation of RBP-Jκ from the cytoplasm to the nucleus.

5.2 Growth Factors

The present invention provides methods that include immortalizing and optionally differentiating precursor cells by activating the Notch pathway in the presence of selected growth factors. Wherein immortalization but not differentiation is to be achieved, the precursor cells of the invention are cultured in the presence of growth factors that support growth but not differentiation. The growth factor can be any type of molecule, such as a protein or a chemical compound, that promotes cellular proliferation and/or survival without substantially causing differentiation.

Generally, the present invention provides methods of growing precursor cells (non-terminally differentiated cells) in culture for a period beyond which the cells would otherwise stop proliferating and/or die by exposing the cell to an agonist of the Notch pathway and one or more growth factors that promotes proliferation but not differentiation of the precursor cells. Exposing the cells to one or more growth factors can initially be done prior to, concurrently with, or following exposure of the cells to a Notch agonist. The precursor cells are concurrently exposed to the growth factor(s) and Notch agonist for at least a portion of the minimal culture time, most preferably the majority of the this time. The minimal culture time is the amount of time at which the cell would die or stop proliferating in the absence of Notch and the selected growth factor(s). In one embodiment, the time period is at least the time period for at least 20 cell division cycles, in another embodiment, and in another embodiment, the time period is at least the time period for 100 cell division cycles. In other embodiments, the time period is at least the time period for 25, 30, 40, 50, 60, 70, 80, or 90 cell division cycles. In yet other embodiments, the time period is at least the time period for 125, 150, 175 or 200 cell division cycles. The amount of time will vary according to cell type and is known to those of skill in the art. For hematopoietic cells, for example, the minimal culture time is 3-4 weeks. In other embodiments, the culture time for hematopoietic cells is 5, 6, 7, 8, 9, or 10 weeks. In yet other embodiments, the culture time for hematopoietic cells is greater than 10 weeks, for example, 12, 15, 18, 20 or 25 weeks.

In specific exemplary embodiments, the precursor cell is a HSC. Stem cell factor (SCF), also known as the c-kit ligand or mast cell growth factor, can be used alone to immortalize a HSC or in combination with one or more of the following growth factors: Flt-3 ligand (Flt-3L), interleukin-6 (IL-6), interleukin-11 (IL-11) and thrombopoietin (Tpo), granulocyte-macrophage colony stimulating factor (GM-CSF), granulocyte colony stimulating factor (G-CSF). The amount of SCF, Flt-3L, IL-6, or Tpo can be in the range of 10-1000 ng/ml, more preferably about 50-500 ng/ml, most preferably about 100-300 ng/ml. In certain specific embodiments, the amount of SCF, Flt-3L, IL-6, or Tpo is 100, 125, 150, 175, 200, 225, 250, 275, 300, 325, 350, 375, 400, 425, or 450 ng/ml. The amount of IL-3, IL-11 G-CSF, or GM-CSF can be in the range of 1-100 ng/ml, more preferably about 5-50 ng/ml. more preferably about 7.5-25 ng/ml, most preferably about 10-15 ng/ml. In certain specific embodiments, the amount of IL-3, IL-11, G-CSF, or GM-CSF is 5, 6, 7, 8, 9, 10, 12.5, or 15 ng/ml. In a preferred embodiment, the foregoing factors are added to HSC in serum free medium.

In a preferred embodiment for immortalizing HSC, the cells are cultured in a tissue culture dish onto which an extracellular matrix protein is bound. In a preferred mode of the embodiment, the extracellular matrix protein is fibronectin (FN), or a fragment thereof. Such a fragment includes but is not limited to CH-296 (Dao et al., 1998, Blood 92(12):4612-21).

In a specific embodiment for immortalizing HSC, the cells are cultured on a plastic tissue culture dish containing immobilized Delta ligand and fibronectin in the presence of 100 ng/ml of each of SCF and TPO, and 10 ng/ml GM-CSF. In another specific embodiment for immortalizing HSC, the cells are cultured on a plastic tissue culture dish containing immobilized Delta ligand and fibronectin in the presence of 100 ng/ml of each of SCF, Flt-3L, Tpo and IL-6 and 10 ng/ml of IL-3. In another specific embodiment for immortalizing HSC, the cells are cultured on a plastic tissue culture dish containing immobilized Delta ligand and fibronectin in the presence of 100 ng/ml of each of SCF and Flt-3L and 10 mg/ml of G-CSF and GM-CSF. In another specific embodiment for immortalizing HSC, the cells are cultured on a plastic tissue culture dish containing immobilized Delta ligand and fibronectin in the presence of 100 ng/ml of each of SCF, Flt-3L and Tpo and 10 mg/ml of GM-CSF. In yet another specific embodiment for immortalizing HSC, the cells are cultured on a plastic tissue culture dish containing immobilized Delta ligand and fibronectin in the presence of 300 ng/ml of each of SCF and Flt-3L, 100 ng/ml of each of Tpo and IL-6, and 10 mg/ml of IL-3. In a highly preferred embodiment for immortalizing HSC, the cells are cultured on a plastic tissue culture dish containing immobilized Delta ligand and fibronectin in the presence of 100 ng/ml of each of SCF, Flt-3L, and Tpo and 10 mg/ml of each of G-CSF and GM-CSF. In alternative embodiments to the foregoing culture conditions, fibronectin is excluded from the tissue culture dishes or is replaced by another extracellular matrix protein.

When differentiation is desired, SCF can be used in combination with GM-CSF or interleukin-7 (IL-7) to differentiate Immortalized HSCs into myeloid stem cells or lymphoid stem cells, respectively. In other embodiments, a retinoic acid receptor (RAR) agonist, most preferably all trans retinoic acid (ATRA) is used to promote the differentiation of an immortalized HSC into a HPP-CFC.

In other embodiments, EGF can be used in conjunction with a Notch agonist to immortalize epithelial and fibroblastic cells, alone or in combination with IGF-1 and TGF-β. In another embodiment, FGF-1 can be used in conjunction with a Notch agonist to immortalize endothelial cells. In yet another embodiment, FGF-2 can be used in conjunction with a Notch agonist to immortalize mesodermal and neurectodermal cells or to differentiate adipocyte and ovarian granulosa cells. In yet other embodiments, FGF-7 can be used in conjunction with a Notch agonist for keratinocyte immortalization and/or differentiation, or prostate epithelial immortalization and/or differentiation. In another embodiment, HGF can be used in conjunction with a Notch agonist to immortalize hepatocytes. In yet another embodiment, IL-6 can be used in conjunction with a Notch agonist to differentiate keratinocytes or neuronal stem and progenitor cells. In yet another embodiment, PDGF can be used in conjunction with a Notch agonist to immortalize mesodermal and neurectodermal cells, alone or in combination with EGF and/or IGF-1. In yet other embodiments, NGF, CNTF, GDNF or BDNF can be used individually or in combination in conjunction with a Notch agonist to immortalize neuronal cells.

The growth factors utilized by the methods of the invention can be obtained commercially, produced by recombinant expression, or chemically synthesized. For example, ATRA, BDNF (human), CNTF (human and rat), EGF (human), FGF-1 (human and bovine), FGF-2 (human and bovine), FGF-7 (human), Flt-3L (human), GDNF (human and rat), HGF (human), IGF-1 (human), IL-6 (human and mouse), IL-11 (human), NGF (murine), PDGF (human AA, AB, and BB isoforms), SCF (human), TGF-β (human), Tpo (human and murine) can be purchased from Sigma (St. Louis, Mo.). EGF (human and murine), FGF-1 (human), FGF-2 (human), GM-CSF (human and murine), IGF-1 (human), IL-6 (human and murine), IL-7 (human and murine), NGF (murine), PDGF (human AA, AB, and BB isoforms), SCF (human) and TGF-β (human) can be purchased from Life Technologies, Inc. (Rockville, Md.).

In other embodiments, the growth factors are produced by recombinant expression (e.g., as described in Section 5.3, infra), or by chemical peptide synthesis (e.g., by a peptide synthesizer). Growth factor nucleic acid and peptide sequences are generally available from GenBank. Exemplary GenBank accession numbers for growth factors (which provide both the nucleic acid sequences and the sequences of the encoded proteins) are provided below:

| Growth Factor | Accession No. of Human Gene | Accession No. of Murine Gene |
|---|---|---|
| EGF | NP_001954.1(protein)/X04571.1(cDNA) | J00380 |
| Epo | X02158 | M12482 |
| FGF-1 | A33665(protein)/AH004637(cDNA) | U67610 |
| FGF-2 | NM_002006 | NM_008006 |
| FGF-7 | M60828 | NM_008008 |
| Flt-3L | U04806 | U04807 |

-continued

| Growth Factor | Accession No. of Human Gene | Accession No. of Murine Gene |
|---|---|---|
| GM-SCF | X03021 | X03020 |
| HGF | P14210(protein)/E03331(cDNA) | D10212 |
| IGF-1 | M29644 | NM_010512 |
| IL-3 | M20137 | K03233 |
| IL-6 | M29150 | M20572 |
| IL-7 | AH006906 | AH001973 |
| IL-11 | M57765 | U03421 |
| NGF | CAA37703(protein)/E03589(cDNA) | AAA37686(protein)/AH001904(cDNA) |
| PDGF | X03795 (A chain) NM_002608 (B chain) | M29464 (A chain) |
| SCF | M59964 | M57647 |
| TGF-β | M60315 | M13177 |
| Tpo | U59494 | L34169 |

Preferably, but not necessarily, the growth factor used to immortalize and optionally differentiate a precursor cell in the presence of a Notch agonist by the methods of the invention is derived from the same species as the precursor cell. The particular growth factor(s) utilized to immortalize or differentiate a precursor cell depends on the precursor cell type, and are well known to those of skill in the art.

The amount or concentration of growth factors suitable for immortalizing a precursor cell or differentiating an immortalized precursor cell will depend on the activity of the growth factor preparation, the species correspondence between the growth factors and the precursor cell, etc. Generally, when the growth factor(s) and the precursor cell are of the same species, the total amount of growth factor in the culture medium ranges from 1 ng/ml to 5 μg/ml, more preferably from 5 ng/ml to 1 μg/ml, and most preferably from about 10 ng/ml to 200 ng/ml. In a preferred embodiment, the precursor cell is a HSC and is immortalized by exposing the cell to a Notch agonist and 100 ng/ml of SCF. In another preferred embodiment, the precursor cell is a HSC and is immortalized by exposing the cell to a Notch agonist and 100 ng/ml of each of Flt-3L, IL-6 and SCF and 10 ng/ml of IL-11. In another preferred embodiment, an immortalized HSC is differentiated into a lymphoid precursor cell by exposing the cell to 100 ng/ml of each of SCF and IL-7. In yet another preferred embodiment, a HSC is differentiated into a myeloid precursor cell by exposing the cell to 100 ng/ml of each of SCF and GM-CSF.

5.3 Recombinant Expression of Notch Agonists and Growth Factors

The present invention provides methods for immortalizing and optionally differentiating precursor cells, said methods comprising culturing precursor cells in the presence of a Notch agonist and selected growth factors. In specific embodiments, the Notch agonist and/or growth factor are recombinantly produced. The Notch agonist or growth factor can be isolated for addition to the cell culture medium in which the precursor cells are cultured, recombinantly expressed in the precursor cell during the immortalization and/or differentiation period, or endogenously or recombinantly expressed in a cell that is cultured together with the precursor cell during the immortalization and/or differentiation period.

Methods for expressing Notch agonists and growth factors are provided herein. The nucleotide sequence coding for a growth factor or growth factor pathway component, for Notch or Notch pathway component, or for a functionally active fragment or other derivative thereof, is referred to in this section as a "Nucleic Acid of Interest", and the protein it encodes the "Protein of Interest". The Nucleic Acid of Interest can be inserted into an appropriate expression vector, i.e., a vector which contains the necessary elements for the transcription and translation of the inserted protein-coding sequence. The necessary transcriptional and translational signals can also be supplied by the native gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding a Protein of Interest thereof may be regulated by a second nucleic acid sequence so that the Protein of Interest is expressed in a host transformed with the recombinant DNA molecule. For example, expression of a Protein of Interest may be controlled by any promoter/enhancer element known in the art. Promoters which may be used to control cell fate control gene or cell fate gene pathway component expression include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); the regulatory sequence of the heat shock protein 70 gene (Bienz and Pelham, 1986, Cell 45:753-60) prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Omitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a preferred embodiment, a method that makes use of a tetracycline-regulated gene expression from $E.\ coli$, referred to as the "Tet system" (Gossen et al., 1995, Science 268:1766-1769; Gossen and Bujard, 1992, Proc. Natl. Acad. Sci. USA 89:5547-5551), is used to direct gene expression. In this case, transgenic cell lines are generated where the coding region for a tetracycline-controlled transcriptional activator (tTA) is operably fused to promoters/enhancers that direct the expression of tTA in a constitutive or inducible manner. The transgenic cell lines are generated where the coding region for the Nucleic Acid of Interest to be mis-expressed is operably fused to a promoter that possesses a tTA-responsive regulatory element. When the cell culture medium is supplemented with a sufficient amount of tetracycline, it completely blocks expression of the gene-of-interest in the resulting progeny. Expression of the gene-of-interest can be induced at will simply by removal of tetracycline from the food or cell culture media. Also, the level of expression of the gene-of-interest can be adjusted by varying the level of tetracycline in the food. Thus, the use of the Tet system as a binary control mechanism for mis-expression has the advantage of providing a means to control the amplitude and timing of mis-expression of the Nucleic Acid of Interest.

Expression vectors containing a Nucleic Acid of Interest can be identified by four general approaches: (a) nucleic acid hybridization; (b) molecular biology, (c) expression of inserted sequences; and (d) presence or absence of "marker" gene functions. In the first approach, the presence of a Nucleic Acid of Interest inserted in an expression vector can be detected by nucleic acid hybridization using probes comprising sequences that are homologous to an inserted Nucleic Acid of Interest. In the second approach, a combination of molecular biology and "marker" gene function are used to identify recombinant expression vectors containing the Nucleic Acid of Interest. For example, if the Nucleic Acid of Interest is inserted into a particular restriction site of an expression vector which codes for both antibiotic resistance, bacterial cells that take up the vector are identified by their resistance to the antibiotic, and those vectors containing the Nucleic Acid of Interest can be identified by restriction digestion of the amplified vector DNA with the particular restriction enzyme. In the third approach, recombinant expression vectors can be identified by assaying the Protein of Interest expressed by the recombinant. Such assays can be based, for example, on the physical or functional properties of the Protein of Interest. In the fourth approach, the vector/host system can be identified based upon the presence or absence of certain "marker" gene functions (e.g. thymidine kinase activity, β-galactosidase, resistance to antibiotics, transformation phenotype, occlusion body formation in baculovirus, etc.)

caused by the insertion of a Nucleic Acid of Interest in the vector. For example, if the Nucleic Acid of Interest is inserted within the marker gene sequence of the vector, recombinants containing the Nucleic Acid of Interest can be identified by the absence of the marker gene function.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g. lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered Protein of Interest may be controlled. Furthermore, different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce large quantities of Delta proteins, as little posttranslational modification is required for their function. Expression in a eukaryotic cell will produce a glycosylated product, which is necessary for some proteins such as Tpo. Expression in metazoan cells can be used to ensure "native" processing of the signal sequences of signaling molecules.

In other specific embodiments, the Protein of Interest may be expressed as a fusion, or chimeric protein product (comprising the peptide, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g. by use of a peptide synthesizer.

Both cDNA and genomic sequences can be cloned and expressed.

The methods described in this section are also applicable to genes and proteins that are not components of the Notch pathway, but to genes and proteins that may be used to indirectly alter the function of a gene or protein of the Notch pathway.

5.4 Precursor Cells

The present invention provides methods for immortalizing and optionally differentiating precursor cells, by circumventing or delaying the entry of the precursor cells into cell cycle arrest or into a nonreplicative phase. Precursor cells for immortalization according to the invention are non-terminally-differentiated cells and can be from any species, including but not limited to human, animal, plant, mammal, primate, mouse, rat, dog, cat, horse, cow, fowl, insect, *Drosophila*, and *C. elegans*. Most preferably, the precursor cells are vertebrate, more preferably mammalian, and most preferably human. In a preferred embodiment, the precursor cells are have not gone through a "crisis" or "senescence" phase resulting in cell line characteristics (e.g. transformation resulting in a stable phenotypic change (see Freshney, 1994, In "Culture of Animal Cells—A manual of Basic Technique," $3^{rd}$ Edition at p. 12, John Wiley & Sons, Inc.). In a preferred embodiment, the precursor cells are primary cells. The term "primary cells" indicates that the cells are have not been through a subculture following their explantation from a tissue source, such as a mammalian subject.

Generally, though not necessarily, the precursor cells are pluripotent stem cells or multipotent progenitor cells. In one embodiment, the precursor cells are stem cells. In another embodiment, the precursor cells are progenitor cells. The precursor cells can be isolated from a cell population, if desired, before or after immortalization. Activation of Notch pathway is preferably achieved by exposing the cell to a Notch ligand, e.g. immobilized on a solid surface in or recombinantly expressed on a cell surface or, or by introducing into the cell a recombinant nucleic acid expressing a dominant active Notch mutant or an activating Notch ligand, or other molecule that activates the Notch pathway.

Most preferably, when the immortalized and/or differentiated progeny of the precursor cells are to be used for repopulation or gene therapy, the precursor cells are obtained directly from tissues of a subject to whom they are administered after immortalizing and, optionally, differentiating. For example, if the precursor cell is a HSC, it can be immortalized following its isolation from a subject by culturing the cell in the presence of a Notch agonist and a combination of IL-6, IL-11, SCF and Flt-3L. In another embodiment, the cell is cultured as described then exposed to SCF and either GM-CSF or IL-7 to stimulate differentiation into myeloid or lymphoid lineages, respectively, then the resulting myeloid or lymphoid cell population transplanted back to the subject. The transplantation is preferably autologous, but can also be non-autologous. For non-autologous transplantation, the recipient is preferably given an immunosuppressive drug to reduce the risk of rejection of the transplanted cell.

The following exemplary embodiments describe approaches which allow for the isolation of precursor cells and precursor cell-containing tissues, which are to be treated with a Notch agonist and growth factors according to the present invention. As already alluded to, isolated cell types or even mixtures of cell populations can be treated according to the method of the invention. If the resulting cell population is to be used for transplantation, a recombinant gene can be introduced into the cell so that it or its progeny expresses a desired gene product before transplantation. Introduction of a recombinant gene can be accomplished either before or after precursor cell expansion and/or differentiation.

In a preferred embodiment, the precursor cell populations are purified or at least highly enriched. However, in order to immortalize and/or differentiate precursor cells by the methods of the present invention it is not necessary that the precursor cells are a pure population. Once a mixture is treated, the desired population can be selected for and purified. Furthermore, purification may not be necessary or desirable prior to therapeutic administration in vivo.

The isolation of precursor cells for use in the present invention can be carried out by any of numerous methods commonly known to those skilled in the art. For example, one common method for isolating precursor cells is to collect a population of cells from a subject and using differential antibody binding, wherein cells of one or more certain differentiation stages are bound by antibodies to differentiation antigens, fluorescence activated cell sorting (FACS) is used to separate the desired precursor cells expressing selected differentiation antigens from the population of isolated cells. FACS is a well-known method for separating particles, including cells, based on the fluorescent properties of the particles (Kamarch, 1987, Methods Enzymol. 151:150-165). Laser excitation of fluorescent moieties in the individual particles results in a small electrical charge allowing electromagnetic separation of positive and negative particles from a mixture.

In another embodiment, magnetic beads can be used to isolate precursor cells from a cell population. Specifically, a magnetic activated cell sorting (MACS) technique may be used. MACS is a method for separating particles based on their ability to bind magnetic beads (0.5-100 µm diameter). Magnetic beads can be obtained from Dynal (Oslo, Norway; http://www.dynal.no). A variety of useful modifications can be performed on the magnetic microspheres, including covalent addition of antibody which specifically recognizes a cell-solid phase surface molecule or hapten. A magnetic field is then applied, to physically manipulate the selected beads. The beads are then mixed with the cells, e.g. the cell population comprising precursor cells, to allow binding. The cells are then passed through a magnetic field to separate out cells having the desired cell surface markers.

In another embodiment, the surface of a culture dish may be coated with antibodies, and used to separate cells by a method called panning. Cells can be incubated successively in separate dishes, each of which is coated with an antibody against a marker of the desired cell type, and rinsed thoroughly following each incubation. The particular combination of antibodies utilized recognizes a corresponding combination of markers that are specific to the desired cell type but not other cell types that are likely to exist in the mixed cell population. Following the final rinse step, the cells left bound to the plate will be cells of the desired cell type.

Immortalized or Differentiated cells can be diluted into separate dishes, such as microtiter dishes, for clonal isolation. Preferably, prior to dilution, cells of the desired cell type may be purified by any method known in the art. For example, the Immortalized or Differentiated cells may be purified by FACS or MACS, as described above. In addition to endogenous markers of the precursor or differentiated cell types, the Immortalized or Differentiated cells may be purified by transfecting the precursor cell with construct encoding a reporter gene under the control of a lineage-specific promoter that is activated in the desired cell type (see e.g. U.S. Pat. No. 5,639,618).

The following section describes exemplary methods for the extraction or isolation of specific types of cells. In addition, any method known in the art can be employed.

5.4.1 Hematopoietic Cells

The methods of the present invention encompass the immortalization and optionally differentiation of any non-terminally differentiated hematopoietic cell, including but not limited to HSCs, lymphoid stem cells and myeloid stem cells. Any technique which provides for the isolation of hematopoietic cells can be used in this embodiment of the invention.

In a preferred embodiment, the hematopoietic cell is a HSC. Techniques by which the isolation of HSCs can be accomplished include the isolation HSCs from bone marrow cells isolated from a donor, or where the progeny of the HSC are to be used for transplantation, the future host. Non-autologous HSC are used preferably in conjunction with a method of suppressing transplantation immune reactions of a future host/subject. In a particular embodiment of the present invention, human bone marrow cells can be obtained from the posterior iliac crest by needle aspiration (see, e.g. Kodo et al., 1984, J. Clin. Invest. 73:1377-1384). In a preferred embodiment of the present invention, the HSCs or their progeny can be made highly enriched or in substantially pure form. This enrichment can be accomplished before, during, or after immortalizing and/or differentiating according to the methods of the present invention.

Another technique for the isolation of HSCs is described by Milner et al., 1994, Blood 83:2057-2062. Bone marrow samples are obtained and are separated by Ficoll-Hypaque density gradient centrifugation, are washed, and stained using two-color indirect immunofluorescent antibody binding and then separated by fluorescence-activated cell sorting (FACS). The cells are labelled simultaneously with IgG antibodies such that $CD34^+$ HSCs, including the immature subset that lacks expression of individual lineage associated antigens, $CD34^+lin^-$, are isolated from the cells collected from marrow.

Where hematopoietic progenitor cells are desired, the presence of hematopoietic progenitor cells and/or their progeny can be detected by commonly known in vitro colony forming assays (e.g., those that detect CFU-GM, BFU-E). As another example, assays for HSCs are also known in the art (e.g., spleen focus forming assays, assays that detect the ability to form progenitors after replating).

5.4.1.1 Hematopoietic Cell Markers

The following markers of hematopoietic cell types can be used to identify hematopoietic cells and to select or enrich the desired hematopoietic cell types (in the precursor cell population or in Immortalized or Differentiated cell populations).

Groups of antibodies have been used to distinguish different cells of the hematopoietic system, based primarily on the differential expression of various cell surface antigens on different hematopoietic cell types. Monoclonal antibodies can be used in conjunction with cell sorting to enrich for hematopoietic cells of choice. For example, human HSCs were initially purified on the basis of CD34 expression and lack of CD38 expression. Using anti-CD34 antibodies, HSCs could be enriched from 1-2% of a normal bone marrow cell population (Civin et al., 1989, Report on the CD34 cluster workshop, In: Leucocyte typing IV, White Cell Differentiation Antigens. Knapp et al., Eds., Oxford University Press. Oxford, p. 818) to approximately 50-80% of the population (Ishizawa et al., In: HSCs: The Mulhouse Manual, Wunder et al., eds. AlphaMed Press, Ohio pp 171-182; Shpall et al., 1994, J. Clinical Oncology 12:28-36; Winslow et al., 1994, Bone Marrow Transplantation 14:265-271; Thomas, 1994, Cancer Research, Therapy and Control 4(2): 119-128). Any combination of antibodies known in the art can be used to identify or select for a desired hematopoietic cell type, either by selection for cells that express antigens present on the cells of interest or by depletion of cells that express unwanted antigens.

In addition to being $CD34^+$, HSCs are preferably $CD33^-$, $CD38^-$, HLA $DR^-$ and Thy-$1^{lo}$ (Craig et al., 1993, J. Exp. Med. 177:1331; Civin et al., 1994, J. Immunol. 133:157; Civin et al., 1987, Exp. Hematol. 15:10; Terstappen et al., 1991, Blood 77:1218). Further, human HSCs are preferably $CD45Ra^-$, $CD19^-$ and c-$kit^+$ (U.S. Pat. No. 5,965,437 to Scadden).

Another HSC marker which can be used to select and/or enrich for HSCs is cells the vascular endothelial growth factor receptor 2 (VEGFR2, also known as KDR; Ziegler et al., 1999, Science 285:1553-1558).

Human hematopoietic progenitor cells and human HSCs also be enriched by incubating a sample such as bone marrow extract with antibodies that recognize glycophorin A, CD3, CD24, CD 16, and CD14 and separating the antibody-bound cells from non-antibody bound cells. Antibodies against CD45RA, CD36, CD56, CD2, CD19, CD66a and CD66b can also be used to refine this process. The non-antibody bound cell population is enriched for hematopoietic stem and progenitor cells (see U.S. Pat. No. 5,877,299 to Thomas and Lansdorp). In other studies, My10 and HLA-DR antibodies have been used in association with two color sorting to obtain highly enriched progenitor cell populations from human marrow (Lu et al., 1987, J. Immunol. 139(6):1823-1829). T lymphocyte depletion can also be used to enrich for hematopoietic stem or progenitor cells. In this procedure, T lymphocytes are selectively removed from the cell population by pretreating cells with a monoclonal antibody(ies), that recognize a T cell antigen, plus complement. Such a procedure has been described previously (Broxmeyer et al., 1984, J. Clin. Invest. 73:939-953).

Glycophorin A antibodies can be used to select for or against erythrocytes. Antibodies against CD14, CD16, CD66a and CD66b can be used to select for or against monocytes. Antibodies against CD24, CD3, CD19, CD20, CD56, CD2 can be used to select for or against B and T lymphocytes and NK cells. Antibodies against CD45RA and CD36 can be used to select for or against T-cells, B-cells, granulocytes, platelets, monocytes, differentiated erythroid precursors, and some committed mature progenitors. See, e.g., U.S. Pat. No. 5,877,299. Other T-cell markers include CD7, CD5, TCD-2, and either CD4 or CD8. CD7 and terminal deoxyribonucleotidyl transferase (Tdt) are markers of pre-T progenitor cells. Additional markers of pre-B progenitor cells are MHC class II antigens. Mature B cells are further characterized by the expression of CD21. See, e.g., Raska and Ponzio, 1994, In "Immunology and Inflammation: Basic Mechanisms and Clinical Consequences," Sigal and Ron, Eds., McGraw-Hill, Inc.

In specific embodiments, antibodies which are currently available and can be used in enrichment protocols include My-10 and 3C5 (which recognize CD34), or RFB-1 (which recognizes CD99 (Petty and Tippett, 1995, Vox Sang 69(3): 231-5) and identifies populations of BFU-E cells (Kannourakis and Johnson, 1988, Blood 71(3):758-65)). Other currently available antibodies against the above-mentioned hematopoietic antigens are disclosed in U.S. Pat. No. 5,877, 299. These antibodies can be used alone or in combination with procedures such as "panning" (Broxmeyer et al., 1983, J. Clin. Invest. 73:939-953) or fluorescence activated cell-sorting (FACS) (Williams et al., 1985, J. Immunol. 135:1004; Lu et al., 1986, Blood 68(1): 126-133) to isolate those cells containing surface determinants recognized by the monoclonal antibodies.

Another method that can be used is that of separating the stem and progenitor cells by means of selective agglutination using a lectin such as soybean (Reisner et al., 1980, Proc. Natl. Acad. Sci. U.S.A. 77:1164). This procedure can be a viable alternative for separation and enrichment of stem and progenitor cells without removal of possibly necessary accessory cells (Reisner et al., 1983, Blood 61(2):341-348; Reisner et al./, 1982, Blood 59(2):360-363).

Theoretically, only one early stem cell is needed for repopulation of the entire hematopoietic system. There is laboratory evidence that under ideal conditions and when the microenvironment nurturing the stem and progenitor cells in the recipient animal is not affected, a single stem cell can entirely repopulate the defective hematopoietic system of a mouse and rescue it from the lethal complications of anemia (Boggs et al., 1982, J. Clin. Invest. 70:242-253). Doubtless, under clinical conditions in man it would generally require more than a single stem cell to rescue the hematopoietic system. Moreover, the presence of accessory or helper cells (non-stem/progenitor cells that influence the growth of stem/progenitor cells), in addition to stem and progenitor cells, may be required (Spooncer et al., 1985, Nature (London) 316:62-64), especially if the microenvironment of the host is injured by treatments such as irradiation or chemotherapy. Thus, while there are ways to separate hematopoietic stem and progenitor cells from other cord blood cells (Leary et al., 1984, J. Clin. Invest. 74:2193-2197) and these and other methods could be used to isolate and store pure or highly enriched preparations of these cells for immortalization and eventually transplantation, caution should be used in attempts at transplanting patients with purified preparations of stem and progenitor cells.

5.4.2 Mesenchymal Stem Cells

One of the most important type of precursor cells for therapeutic applications are those derived from the mesenchyme. Mesenchymal stem cells are pluripotent cells found in the bone marrow, blood, dermis, and periosteum that are capable of differentiating into cells of various lineages (e.g., steogenic, chondrogenic, tendonogenic, adipogenic, myogenic lineages, etc.) depending on the in vitro or in vivo microenvironment. (Caplan, 1991, J. Orth. Res. 641-650). Most work to date involves the isolation and culture of cells which can differentiate into chondrocytes and osteoblasts. The systems developed to isolate the relevant progenitor cell populations were worked out first in chick embryos (Caplan, 1970, Exp. Cell. Res. 62:341-355; Caplan, 1981, 39th Annual Symposium of the Society for Developmental Biology, pp. 37-68; Caplan et al., 1980, Dilatation of the Uterine Cervix 79-98; DeLuca et al., 1977, J. Biol. Chem. 252:6600-6608; Osdoby et al., 1979, Dev. Biol. 73:84-102; Syftestad et al., 1985, Dev. Biol. 110:275-283).

Caplan et al., 1993, and Caplan et al., 1996, U.S. Pat. Nos. 5,226,914 and 5,486,359 respectively, describe exemplary methods for isolating mesenchymal stem cells from bone marrow. These isolated marrow stem cells can be immortalized using a Notch agonist and growth factors that promote proliferation but not differentiation. These precursor cells, may then be further differentiated, e.g. by growing in the presence of growth factors that promote differentiation. The cells are preferably differentiated into osteocytes, cartilage, chondrocytes, adipocytes, etc.

Several bone marrow isolation protocols have been reported and can be used to obtain precursor cells. Single cell suspensions from rat bone marrow can be prepared according to Goshima et al., 1991, Clin. Orth. and Rel. Res. 262:298-311. Human stem cell cultures from marrow can be prepared as described by Bab et al., 1988, Bone Mineral 4:373-386 as follows: Whole marrow cells are obtained from subjects. The marrow samples are separated from either the iliac crest or femoral midshaft. Marrow samples, 3 ml in volume, are transferred to 6 ml of serum-free Minimal Essential Medium (MEM) containing 50 U/ml penicillin and 0.05 mg/ml streptomycin-sulfate. A suspension of predominantly single cells is prepared as described previously (Bab et al., 1984, Calcif. Tissue Int. 36:77-82; Ashton et al., 1984, Calcif. Tissue Int. 36:83-86) by drawing the preparation into a syringe and expelling it several times sequentially through 19, 21, 23 and 25 gauge needles. The cells are counted using a fixed volume hemocytometer and the concentration adjusted to $1-5 \times 10^8$ total marrow cells per ml suspension. Positive and negative control cell suspensions can be set as described before (Shteyer et al., 1986, Calcif. Tissue Int. 39:49-54), using rabbit whole marrow and spleen cells, respectively.

5.4.3 Fibroblasts

Connective tissue comprises fibroblasts, cartilage, bone, adipose and smooth muscle cells. Fibroblasts are the least differentiated of the connective tissue cells and are dispersed in connective tissues throughout the body. They can be identified by their characteristic secretion of type I and/or type III collagen. Fibroblasts can migrate into tissue wounds and secrete a collagenous matrix that heals and isolates the wounds. Further, they can differentiate into other members of the connective tissue family, depending on their local cues. Fibroblasts can be isolated from a variety of different tissues, including but not limited to the bone marrow stroma, according to methods known to those of ordinary skill in the art.

5.4.4 Neural Stem Cells

It is generally assumed that neurogenesis in the central nervous system ceases before or soon after birth. In recent years, several studies have presented evidence indicating that at least to some degree new neurons continue to be added to the brain of adult vertebrates (Alvarez-Buylla and Lois, 1995, Stem Cells (Dayt) 13:263-272). The precursors are generally located in the wall of the brain ventricles. It is thought that from these proliferative regions, neuronal precursors migrate towards target positions where the microenvironment induces them to differentiate. Studies have been reported where cells from the sub-ventricular zone can generate neurons both in vivo as well as in vitro, reviewed in Alvarez-Buylla and Lois, 1995, Stem Cells (Dayt) 13:263-272.

The neuronal precursors from the adult brain can be used as a source of cells for neuronal transplantation (Alvarez-Buylla, 1993, Proc. Natl. Acad. Sci. USA 90:2074-2077). Neural crest cells have also been long recognized to be pluripotent neuronal cells which can migrate and differentiate into different cell neuronal cell types according to the instructions they receive from the microenvironment they find themselves in (LeDouarin and Ziller, 1993, Curr. Opin. Cell Biol. 5:1036-1043).

5.4.5 Fetal Cells

In certain embodiments of the present invention, precursor cells can be fetal cells, e.g., for culturing until required at a later point in life. Fetal blood can be obtained by any method known in the art. For example, fetal blood can be taken from the fetal circulation at the placental root with the use of a needle guided by ultrasound (Daffos et al., 1985, Am. J. Obstet. Gynecol. 153:655-660; Daffos et al., 1983, Am. J. Obstet. Gynecol. 146:985), by placentocentisis (Valenti, 1973, Am. J. Obstet. Gynecol. 115:851; Cao et al., 1982, J. Med. Genet. 19:81), by fetoscopy (Rodeck, 1984, in Prenatal Diagnosis, Rodeck, C. H. and Nicolaides, K. H., eds., Royal College of Obstetricians and Gynecologists, London), etc. In certain embodiments, fetal cells are obtained form umbilical cord blood, placental blood or Wharton's jelly. Wharton's jelly is a gelatinous substance found in the umbilical cord which has been generally regarded as a loose mucous connective tissue, and has been frequently described as consisting of fibroblasts, collagen fibers and an amorphous ground substance composed mainly of hyaluronic acid (Takechi et al., 1993, Placenta 14:235-45).

Alternatively, the precursor cells of the invention can be obtained from neonatal blood. Neonatal blood can preferably be obtained by direct drainage from the cord and/or by needle aspiration from the delivered placenta at the rot and at distended veins.

Collections should be made under sterile conditions. Immediately upon collection, the neonatal or fetal blood should be mixed with an anticoagulant. Such an anticoagulant can be any known in the art, including but not limited to CPD (citrate-phosphate-dextrose), ACD (acid citrate-dextrose), Alsever's solution (Alsever and Ainslie, 1941, N.Y. St. J. Med. 41:126), DeGowin's Solution (DeGowin et al., 1940, J. Am. Med. As. 114:850), Edglugate-Mg (Smith et al., 1959, J. Thorac. Cardiovasc. Surg. 38:573), Rous-Turner Solution (Rous and Turner, 1916, J. Exp. Med. 23:219), other glucose mixtures, heparin, ethyl biscoumacetate, etc. (See, Hurn, 1968, Storage of Blood, Academic Press, New York, pp. 26-160).

Primary cultures of human fetal brain cells can be isolated from human fetuses, obtained from legal abortions after 5 to 12 weeks of gestation. Expulsion can be done by syringe-driven gentle aspiration under echographic control.

5.4.6 Epithelial Stem Cells and Keratinocytes

Epithelial stem cells (ESCs) and keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of precursor cells within the germinal layer, the layer closest to the basal lamina. Precursor cells within the lining of the gut provide for a rapid renewal rate of this tissue. ESCs obtained from the skin or lining of the gut of a subject or donor (Rheinwald, 1980, Meth. Cell Bio. 21A:229; Pittelkow and Scott, 1986, Mayo Clinic Proc. 61:771) can be immortalized according to the methods of the present invention.

5.4.7 Liver Stem Cells

Liver stem cells can be isolated by methods described in PCT Publication WO 94/08598, dated Apr. 28, 1994.

5.4.8 Kidney Stem Cells

Mammalian kidney emerges from the metanephric mesenchyme which induces the uteric bud to undergo a series of morphogenetic movements ultimately forming the mature urinary collecting system (Nigam and Brenner, 1992, Curr. Opin. Nephrol. Huper 1:187-191. The uteric bud, an epithelial outgrowth of the Wolfian duct, contracts and induces condensing adjacent mesenchyme along differentiation pathways of epithelial divergence in early embryonic life. Attempts to study this process in vitro have been reported; metanephros in organ culture can be induced to form tubules using embryonic spinal cord as the inducer. While the specific transducing agents that lead to the induction of metanephric mesenchyme by the uteric bud in vivo or by spinal cord in vitro are not known, cell specific markers show that the differentiation program is induced in progenitor cells (Karp et al., 1994, Dev. Biol. 91:5286-5290).

5.5 Differentiation of Precursor Cells

The present invention provides methods for the differentiation of precursor cells before, after or concurrently with their immortalization according to the methods of the present invention. Differentiation of precursor cells is accomplished by exposing the cells to one or growth factors that promote differentiation, and growing the cells under conditions that allow differentiation to take place. The growth factors for differentiating precursors cells or their Immortalized progeny include those described in section 5.2, supra. The selection of growth factors that promote the differentiation of precursor cells depends on the precursor cell types, and are known to those of skill in the art. For example, as described in section 5.2, an Immortalized HSC is differentiated into a lymphoid stem cell by exposing the cell to 100 ng/ml of each of SCF and IL-7, and into a myeloid stem cell by exposing the cell to 100 ng/ml of each of SCF and GM-CSF. In certain instances, a growth factor may be used for both differentiation and proliferation by combining it with different growth factors; for example SCF can be used alone or in combination with IL-6, IL-11, and Flt-3L to immortalize HSCs (by exposing the HSCs to SCF (and optionally IL-6, IL-11, and Flt-3L) and a Notch agonist for a time period beyond which the HSCs would normally stop proliferating and/or die), and in combination with IL-7 or GM-CSF to promote the differentiation of Immortalized HSCs into lymphoid stem cells or myeloid stem cells, respectively.

5.6 Therapeutic Uses of the Cultured Cells of the Invention

The present invention provides methods that allow the immortalization and, optionally, differentiation of precursor cells. In certain embodiments, the resulting cells are used for cell therapy. By way of example and not limitation, the following sections describe exemplary embodiments for the treatment of hematopoietic disorders and injury to nervous tissue using the cells produced by the methods of the invention. However, the Immortalized or Differentiated cells may be useful for replenishing any deficient cell populations or supply therapeutic cell populations of the precursor cell type or as gene therapy vectors (see Section 5.12, infra). Additionally, precursor cells can be preserved, e.g. by freezing, prior to or following immortalization (see Section 5.7, infra).

5.6.1 Hematopoietic Disorders

Transplantation of Immortalized HSCs or Differentiated hematopoietic cells may be useful in the treatment or prevention of hematopoietic disorders and diseases. In one embodiment, the Immortalized or Differentiated cells are used to treat or prevent a hematopoietic disorder or disease characterized by a failure or dysfunction of normal blood cell production and maturation cell. In another embodiment, the Immortalized or Differentiated cells are used to treat or prevent a hematopoietic disorder or disease resulting from a hematopoietic malignancy. In yet another embodiment, the Immortalized or Differentiated cells are used to treat or prevent a hematopoietic disorder or disease resulting from immunosuppression, particularly immunosuppression in subjects with malignant, solid tumors. In yet another embodiment, the Immortalized or Differentiated cells are used to treat or prevent an autoimmune disease affecting the hematopoietic system. In yet another embodiment, the Immortalized or Differentiated cells are used to treat or prevent a genetic or congenital hematopoietic disorder or disease. The type of Differentiated cells used in the treatment of a hematopoietic disease or disorder in a subject is chosen to ameliorate the subject's condition, for example cells differentiated along the erythrocytic pathways to treat anemia.

Examples of particular hematopoietic diseases and disorders which can be treated by the Immortalized and/or by the Differentiated cells of the invention include but are not limited to those listed in Table 1, infra.

TABLE I

DISEASES OR DISORDERS WHICH CAN BE TREATED BY HEMATOPOIETIC RECONSTITUTION WITH NEONATAL STEM AND PROGENITOR CELLS

I. Diseases Resulting from a Failure or Dysfunction of Normal Blood Cell Production and Maturation
   hyperproliferative stem cell disorders
   aplastic anemia
   pancytopenia
   agranulocytosis
   thrombocytopenia
   red cell aplasia
   Blackfan-Diamond syndrome due to drugs, radiation, or infection
   idiopathic
II. Hematopoietic malignancies
   acute lymphoblastic (lymphocytic) leukemia
   chronic lymphocytic leukemia
   acute myelogenous leukemia
   chronic myelogenous leukemia
   acute malignant myelosclerosis
   multiple myeloma
   polycythemia vera
   agnogenic myelometaplasia
   Waldenstrom's macroglobulinemia
   Hodgkin's lymphoma
   non-Hodgkin's lymphoma
III. Immunosuppression in patients with malignant, solid tumors
   malignant melanoma
   carcinoma of the stomach
   ovarian carcinoma
   breast carcinoma
   small cell lung carcinoma
   retinoblastoma
   testicular carcinoma
   glioblastoma
   rhabdomyosarcoma
   neuroblastoma
   Ewing's sarcoma
   lymphoma
IV. Autoimmune diseases
   rheumatoid arthritis
   diabetes type I
   chronic hepatitis
   multiple sclerosis
   systemic lupus erythematosus
V. Genetic (congenital) disorders
   anemias
   familial aplastic
   Fanconi's syndrome
   Bloom's syndrome
   pure red cell aplasia (PRCA)
   dyskeratosis congenita
   Blackfan-Diamond syndrome
   congenital dyserythropoietic syndromes I-IV
   Chwachmann-Diamond syndrome
   dihydrofolate reductase deficiencies
   formamino transferase deficiency
   Lesch-Nyhan syndrome
   congenital spherocytosis
   congenital elliptocytosis
   congenital stomatocytosis
   congenital Rh null disease
   paroxysmal nocturnal hemoglobinuria
   G6PD (glucose-6-phosphate dehydrogenase) variants 1, 2, 3
   pyruvate kinase deficiency
   congenital erythropoietin sensitivity deficiency
   sickle cell disease and trait
   thalassemia alpha, beta, gamma
   met-hemoglobinemia
   congenital disorders of immunity
   severe combined immunodeficiency disease (SCID)
   bare lymphocyte syndrome
   ionophore-responsive combined immunodeficiency
   combined immunodeficiency with a capping abnormality TABLE I-continued DISEASES OR DISORDERS WHICH CAN BE TREATED
BY HEMATOPOIETIC RECONSTITUTION WITH NEONATAL
STEM AND PROGENITOR CELLS nucleoside phosphorylase deficiency
    granulocyte actin deficiency
    infantile agranulocytosis
    Gaucher's disease
    adenosine deaminase deficiency
    Kostmann's syndrome
    reticular dysgenesis
    congenital leukocyte dysfunction syndromes
VI. Others
    osteopetrosis
    myelosclerosis
    acquired hemolytic anemias
    acquired immunodeficiencies
    infectious disorders causing primary or secondary
    immunodeficiencies
    bacterial infections (e.g., Brucellosis, Listerosis, tuberculosis, leprosy)
    parasitic infections (e.g., malaria, Leishmaniasis)
    fungal infections
    disorders involving disproportions in lymphoid cell sets and
    impaired immune functions due to aging
    phagocyte disorders
    Kostmann's agranulocytosis
    chronic granulomatous disease
    Chediak-Higachi syndrome
    neutrophil actin deficiency
    neutrophil membrane GP-180 deficiency
    metabolic storage diseases
    mucopolysaccharidoses
    mucolipidoses
    miscellaneous disorders involving immune mechanisms
    Wiskott-Aldrich Syndrome
    α1-antitrypsin deficiency In one embodiment, the Immortalized or Differentiated cells are administered to a subject with a hematopoietic deficiency. In one mode of the embodiment, the Immortalized or Differentiated cells are administered prenatally to a fetus diagnosed with a hematopoietic deficiency.

Hematopoietic deficiencies whose treatment with the Immortalized or Differentiated cells of the invention is encompassed by the methods of the invention include but are not limited to decreased levels of either myeloid, erythroid, lymphoid, or megakaryocyte cells of the hematopoietic system or combinations thereof, including those listed in Table 1. The type of Differentiated cells used in the treatment or prevention of a hematopoietic disease or disorder is selected so that it complements the subject's hematopoietic deficiency; for example, Immortalized HSCs that have been differentiated along a lymphocytic pathway are used to treat an individual with AIDS.

Among conditions susceptible to treatment with the cell lines of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g. exposure to chemotherapeutic drugs, radiation and of infection or hemorrhage.

Immortalized HSCs or Differentiated hematopoietic cells may also be useful in the treatment or prevention of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome, myelofibrosis, thrombocytopenia. Severe thrombocytopenia may result from genetic defects such as Fanconi's Anemia, Wiskott-Aldrich, or May-Hegglin syndromes and from chemotherapy and/or radiation therapy or cancer. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Thrombocytopenia may also result from marrow invasion by carcinoma, lymphoma, leukemia or fibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenyloin or carbamazepine, antithyroids such as propylthiouracil and methimazole and diuretics. Transplantation of Immortalized HSCs may be useful in preventing or treating the bone marrow suppression or hematopoietic deficiencies which often occur in subjects treated with these drugs.

Hematopoietic deficiencies may also occur as a result of viral, microbial or parasitic infections and as a result of treatment for renal disease or renal failure, e.g., dialysis. Transplantation of immortalized HSCs may be useful in treating such hematopoietic deficiency.

Various immunodeficiencies e.g., in T and/or B lymphocytes, or immune disorders, e.g., rheumatoid arthritis, may also be beneficially affected by treatment with the Immortalized HSCs. Immunodeficiencies may be the result of viral infections (including but not limited to HIV, HTLVI, HTLVII, HTLVIII), severe exposure to radiation, cancer therapy or the result of other medical treatment.

5.6.2 Treatment of Nervous System Disorders and Injuries

Nervous system disorders involving cell types that require supplementation or replacement and can replenished by transplantation of an Immortalized or Differentiated cell can be treated by the methods of the invention. These include but are not limited to nervous system injuries, and diseases or disorders which result in either a disconnection of axons, a diminution or degeneration of neurons, or demyelination. Nervous system lesions which may be treated in a subject (including human and non-human mammalian subjects) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

It will be understood to those skilled in the art that the above embodiments are merely exemplary; the Immortalized and/or Differentiated cells of the invention or the progeny thereof may be used in the treatment of disease that requires cell or tissue supplementation.

5.7 Preservation of Precursor Cells

In certain embodiments, the precursor cells of the invention are preserved (i) prior to immortalization and optionally differentiation, or (ii) following immortalization and optionally differentiation, while maintaining the integrity of both the cells and their genomes.

In a preferred embodiment, precursor cells are preserved by cryopreservation. Freezing is destructive to most living cells. Upon cooling, as the external medium freezes, cells equilibrate by losing water, thus increasing intracellular solute concentration. Below about 10°-15° C., intracellular freezing will occur. Both intracellular freezing and solution effects are responsible for cell injury (Mazur, 1970, Science 168:939-949). Accordingly, precursor cells are preferably cryopreserved using the methods that have been established to circumvent cellular damage upon freezing living cells, for example the use of cryoprotective agents and optimal cooling rates (Meryman et al., 1977, Cryobiology 14:287-302).

Precursor, Immortalized and Differentiated cells can also be preserved by freeze-drying (reviewed by Simione, 1992, J. Parenter. Sci. Technol. 46(6):226-32).

Because cryopreservation is less damaging that freeze-drying, master stocks are usually maintained at liquid nitrogen or comparable temperatures, while working stocks can be frozen or freeze-dried.

5.8 Screening for Modulators of the Notch Pathway

The present invention provides methods of screening or "screening assays" for identifying modulators of Notch pathway activity. The screening assays of the invention are directed to identifying modulators that include but are not limited to peptides, peptidomimetics, small molecules or other drugs. In certain embodiments, the invention provides methods to screen for modulators that promote or agonize Notch pathway activity. In yet other embodiments, the invention provides methods to screen for modulators that inhibit or antagonize Notch pathway activity.

In certain embodiments, screening for a Notch agonist comprises culturing a non-immortalized precursor cell in the presence of a test molecule and one or more growth factors for a time period beyond which cells of said precursor cell type not in the presence of a Notch agonist and said growth factors stop proliferating and/or die, and detecting whether or not said cells proliferate without terminally differentiating. The ability of the precursor cell or its progeny to proliferate but not terminally differentiate during this time period is indicative that the test molecule is a Notch agonist.

In other embodiments, screening for a Notch antagonist comprises culturing a non-immortalized precursor cell in the presence of a test molecule, a Notch agonist and one or more growth factors for a time period beyond which cells of said precursor cell type not in the presence of said Notch agonist and said growth factors stop proliferating and/or die, and detecting whether or not said cells proliferate without terminally differentiating. A failure of the precursor cell or its progeny to proliferate during this time period that is rescued by the addition of a higher amount of Notch agonist is indicative that the test molecule is a Notch antagonist. The rescue assay excludes those molecules that are antagonists of growth factor pathways. Alternatively, the use of multiple growth factors may circumvent such false antagonists by ensuring that multiple signaling pathways mediate the growth factor signals. Alternatively, a secondary screen may be utilized to determine if the failure to immortalize the precursor cell is mediated through Notch inhibition, for example an assay for the expression of a Notch target reporter gene or the subcellular localization of RBP-Jκ, can indicate whether the Notch pathway or a growth factor signaling pathway is being antagonized. In another embodiment, a secondary screen may entail repeating the assay in the presence of an excess amount of Notch agonist to determine if this rescues the failure to immortalize the precursor cell.

In addition to providing screens for Notch agonists and antagonists, the invention provides methods of screening for a growth factor that promotes proliferation but not differentiation of a precursor cell, comprising culturing a non-immortalized precursor cell in the presence of a test molecule and a Notch agonist for a time period beyond which cells of said precursor cell type not in the presence of said Notch agonist and one or more growth factors that promote proliferation but not differentiation of said precursor cell stop proliferating and/or die, and detecting whether or not said cells proliferate without terminally differentiating. The ability of the precursor cell or its progeny to proliferate but not terminally differentiate during this time period is indicative that the test molecule is a growth factor that promotes proliferation but not differentiation of the precursor cell.

The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145).

Examples of methods for the synthesis of molecular libraries can be found in the art, for example in: DeWitt et al., 1993, Proc. Natl. Acad. Sci. USA 90:6909; Erb et al., 1994, Proc. Natl. Acad. Sci. USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994, J. Med. Chem. 37:1233.

Libraries of compounds may be presented in solution (e.g., Houghten, 1992, Bio/Techniques 13:412-421), or on beads (Lam, 1991, Nature 354:82-84), chips (Fodor, 1993, Nature 364:555-556), bacteria (U.S. Pat. No. 5,223,409), spores (U.S. Pat. Nos. 5,571,698; 5,403,484; and 5,223,409), plasmids (Cull et al., 1992, Proc. Natl. Acad. Sci. USA 89:1865-1869) or phage (Scott and Smith, 1990, Science 249:386-390; Devlin, 1990, Science 249:404-406; Cwirla et al., 1990, Proc. Natl. Acad. Sci. USA 87:6378-6382; and Felici, 1991, J. Mol. Biol. 222:301-310).

5.9 Screening for Genes Involved in Differentiation Processes

The present invention further provides methods of screening for genes that are differentially expressed between precursor cells and their more differentiated progeny, by comparing gene expression profiles of the precursor cells with the gene expression profiles of the more differentiated progeny. The precursor cells are grown according to the methods of the present invention then stimulated to differentiate into more specialized cell types by any method known in the art, including the methods described herein. The gene expression profiles of the precursor cells and their more differentiated progeny cells can be determined by detecting, or more preferably measuring, mRNA or protein levels in both cell types. In certain embodiments, multiple measurements are made to assess the gradual changes in gene expression upon cellular differentiation, for example to distinguish between early and late genes activated in response to the differentiation cues. The methods provided herein allow the identification of genes whose expression is activated in the differentiation process, as well as those whose expression is inhibited. Once a gene associated with cellular differentiation is identified, further studies known to those of skill in the art, including but not limited to genetic manipulation of gene expression (i.e. mutating or knocking out the gene, overexpression of the gene) can be determinative of the gene's role in the process, i.e. whether the induction or inhibition of its expression is necessary and/or sufficient for the differentiation process, or merely indicative of it.

Methods of gene expression profiling to identify genes whose expression is altered during cellular differentiation are well-known to one skilled in the art, and include but are not limited to differential display, serial analysis of gene expression (SAGE), nucleic acid array technology, subtractive hybridization, proteome analysis and mass-spectrometry of two-dimensional protein gels. The methods of gene expression profiling are exemplified by the following references describing differential display (Liang and Pardee, 1992, Science 257:967-971), proteome analysis (Humphery-Smith et al., 1997, Electrophoresis 18:1217-1242; Dainese et al., 1997, Electrophoresis 18:432-442), SAGE (Velculescu et al., 1995, Science 270:484-487), subtractive hybridization (Wang and Brown, 1991, Proc. Natl. Acad. Sci. U.S.A. 88:11505-11509), and hybridization-based methods of using nucleic acid arrays (Heller et al., 1997, Proc. Natl. Acad. Sci. U.S.A. 94:2150-2155; Lashkari et al., 1997, Proc. Natl. Acad. Sci. U.S.A. 94:13057-13062; Wodicka et al., 1997, Nature Biotechnol. 15: 1259-1267).

5.10 Functional Genomics

The Immortalized cells of the invention, or precursor cells undergoing immortalization by the methods taught herein, can be used to practice functional genomics. As used herein, functional genomics refers to using global approaches, such as the genomics and/or proteomics techniques described in Section 5.9, supra, to understand the functions of genes and proteins. Generally, the Immortalized cells or their precursors can be perturbed in small, genetically defined ways and resulting gene expression profiles compared.

In certain embodiments, the Immortalized cells can be used to investigate the role of a gene that is involved in normal or abnormal differentiation processes in a cell, as well as the function of a gene involved in the maintenance of the normal state or that contributes to a diseased state in a cell. In one non-limiting example, the Immortalized cells can be used to study the function of a gene involved in carcinogenesis but is not sufficiently transforming to transform a precursor cell in culture. In another non-limiting example, the Immortalized cells can be used to study the function of a gene involved in the differentiation process. The effect of various polymorphisms on gene activity can also be determined. Immortalized cells can be transfected with a nucleic acid construct that drives the expression of such a gene of interest so that its effects on the cells can be analyzed, for example by profiling gene expression in the cells in the presence or absence of the gene. A large number of potential target genes can be analyzed by such methods. For example, human probe arrays comprising 280,000 different oligonucleotide probes, representing 6,800 human genes, in an area of 1.28×1.28 cm, have been reported. Nucleic acid arrays representing 4,000 common single nucleotide polymorphisms (SNPs) across the human genome have also been reported (Fields et al., 1999, Proc. Natl. Acad. Sci. USA 96:8825-8826).

The studies encompass comparative gene expression or protein profiling between a cell that is normal or mutant for a give gene of interest (the mutant cell can be derived from a knockout transgenic animal, or from a normal animal harboring an antisense construct, or by any of the methods described in Section 5.11, infra).

Such comparative studies allow the identification and validation of drug targets, identifying mutations which impact upon key physiological pathways, genetic/phenotypic analysis, and the effect of different allelic mutations, for example in relation to different prognosis/outcomes in certain disease states. Inferences about functions of related genes expressed at, for example, certain timepoints during differentiation or carcinogenesis, can be improved by clustering algorithms that group profiles of similarly expressed genes. Cluster analysis of gene expression profiles further helps in the identification of common regulatory elements that direct the expression of genes under particular conditions, for example genes that are activated at certain developmental stages.

5.10.1 Exemplary Embodiment: Analysis of Oncogene Function

An exemplary gene of interest is the leukemogenic fusion gene AML1-ETO, which arises as a result of a chromosomal translocation at t(8; 21)(q22;q22) in acute myeloblastic leukemias (AML)(Downing et al., 1993, Blood 81:2860-2865). The AML1-ETO fusion protein is a dominant inhibitor of transcriptional activation function of the normal AML1B protein (Meyers et al., 1995, Mol. Cell. Biol. 15:1974-1982). Because binding sites for the AML1B protein are present on a variety of different myeloid and lymphoid enhancers yet AML1B is insufficient to induce the differentiation of myeloid and lymphoid precursors into myeloid and lymphoid cells types, and because AML1B synergizes with at least one other transcription factor to activate transcription of the gene encoding neutrophil protein 3 (NP3), it has also been suggested that AML1-ETO contributes to leukemogenesis by inhibiting the activity of multiple transcription factors required for cellular differentiation (Westendorf et al., 1998, Mol. Cell. Biol. 18:322-333). The precise activity of AML1-ETO is still not known, however, and Immortalized HSCs can be used to investigate the leukemogenic activity of this protein. For example, Immortalized HSCs that recombinantly express AML1-ETO can be treated with SCF and one of IL7 and GM-CSF as described above to determine whether AML1-ETO on its own is sufficient to block their differentiation along lymphoid or myeloid paths, respectively, and if so, the mechanism by which it does so.

5.11 Disruption or Inhibition of Gene Expression or Activity

In certain embodiments, the present invention entails the use of a precursor or Immortalized cell in which the function of a Gene of Interest has been disrupted or inhibited, for example to identify the effect of gene disruption on the gene expression profile of the cell. The disruption or inhibition of the Gene of Interest can be achieved by any method in the art.

In one embodiment, the disruption or inhibition of the Gene of Interest is achieved by the use of antisense nucleic acids which will prevent the expression of the Gene of Interest The antisense nucleic acids are of at least six nucleotides and are preferably oligonucleotides (ranging from 6 to about 50 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g. Letsinger et al., 1989, Proc. Natl. Acad. Sci. U.S.A. 86:6553-6556; Lemaitre et al., 1987, Proc. Natl. Acad. Sci. 84:648-652; PCT Publication No. WO 88/09810, published Dec. 15, 1988), hybridization-triggered cleavage agents (see, e.g., Krol et al., 1988, BioTechniques 6:958-976) or intercalating agents (see, e.g. Zon, 1988, Pharm. Res. 5:539-549).

In a preferred aspect of the invention, an antisense oligonucleotide is preferably a single-stranded DNA. The oligonucleotide may be modified at any position on its structure with substituents generally known in the art.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide can also comprise at least one modified sugar moiety selected from the group including but not limited to arabinose, 2-fluoroarabinose, xylulose, and hexose.

The antisense oligonucleotide can also comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The antisense oligonucleotide can also be an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641).

Such oligonucleotides may be synthesized by standard methods known in the art, e.g. by use of an automated DNA synthesizer (such as are commercially available from Biosearch, Applied Biosystems, etc.). As examples, phosphorothioate oligos may be synthesized by the method of Stein et al. (1988, Nucl. Acids Res. 16:3209), methylphosphonate oligos can be prepared by use of controlled pore glass polymer supports (Sarin et al., 1988, Proc. Natl. Acad. Sci. U.S.A. 85:7448-7451), etc.

In a specific embodiment, an antisense oligonucleotide comprises catalytic RNA, or a ribozyme (see, e.g., PCT International Publication WO 90/11364, published Oct. 4, 1990; Sarver et al., 1990, Science 247:1222-1225). In another embodiment, the oligonucleotide is a 2'-0-methylribonucleotide (Inoue et al., 1987, Nucl. Acids Res. 15:6131-6148), or a chimeric RNA-DNA analogue (Inoue et al., 1987, FEBS Lett. 215:327-330).

In a specific embodiment, an antisense nucleic acid comprises a double stranded RNA, utilizing a method called RNA interference (or RNA-i), in which injection of a few copies of a double stranded RNA molecules in a cell interferes with the function of an endogenous gene.

In an alternative embodiment, antisense nucleic acids are produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Such promoters include but are not limited to: the SV40 early promoter region (Bemoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), a heat shock enhancer element in the context of a basal promoter such as the heat shock protein 70 gene promoter (Bienz et al., 1986, Cell. 45:753-60), etc.

The antisense nucleic acids of the invention comprise a sequence complementary and hybridizable to at least a sequence-specific portion of an RNA transcript of a Gene of Interest. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a specific RNA it may contain and still form a stable duplex (or triplex, as the case may be). One skilled in the art can ascertain a tolerable degree of mismatch by use of standard procedures to determine the melting point of the hybridized complex.

Other methods of inhibiting the Gene of Interest include, but are not limited to, the use of antibodies which block the activity of the Gene of Interest. Such antibodies can be polyclonal, monoclonal, chimeric, single chain, Fab fragments, or from an Fab expression library.

Various procedures known in the art may be used for the production of polyclonal antibodies to a Gene of Interest. For the production of polyclonal antibody, various host animals can be immunized by injection with the native protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhold limpet hemocyanins, dinitrophenol, and potentially useful human adjuvants such as BCG (bacille Calmette-Guerin) and *corynebacterium parvum*.

For preparation of monoclonal antibodies, any technique which provides for the production of antibody molecules by continuous cell lines in culture may be used. For example, the hybridoma technique originally developed by Kohler and Milstein (1975, Nature 256, 495-497), as well as the trioma technique, the human B-cell hybridoma technique (Kozbor et al., 1983, Immunology Today 4, 72), and the EBV-hybridoma technique to produce human monoclonal antibodies (Cole et al., 1985, in Monoclonal Antibodies and Cancer Therapy, Alan R. Liss, Inc., pp. 77-96).

Antibody fragments which contain the idiotype (binding domain) of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay).

In another specific embodiment, an inhibitor of the Gene of Interest is a peptidomimetic or peptide analog of the protein encoded by the Gene of Interest, that would inhibit the activity of the protein by competing for its interaction with other molecules. Such an inhibitor can be identified by binding assays selected from among those known in the art.

In another embodiment, the Gene of Interest is disrupted by gene targeting, which is a method of using homologous recombination to modify a mammalian genome. The Immortalized cell can be derived from an animal with the Gene of Interest disrupted in the germline, after the Gene of Interest is targeted in embryonic stem (ES) cells. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. The targeting constructs are typically arranged so that they insert additional sequences, such as a positive selection marker, into coding elements of the target gene, thereby functionally disrupting it. Targeting constructs usually are insertion-type ("knock in") or replacement-type constructs ("knock out"; Hasty et al., 1991, Mol. Cell. Biol. 11:4509).

If the animal harboring a targeted disruption in a Gene of Interest is not viable, the targeted disruption can be made conditional or tissue-specific, for example by use of the Cre-Lox system or the TetR system. Wherein the disruption in the Gene of Interest is desired to be temporally or developmentally regulated, the Cre-Lox system may be employed. The Cre-Lox system may be used to activate or inactivate the Gene of Interest at a specific developmental stage or in a particular tissue. Generally, methods utilizing Cre-Lox technology are carried out as described by Torres and Kuhn, 1997, "Laboratory Protocols for Conditional Gene Targeting", Oxford University Press. Methodology similar to that described for the Cre-Lox system can be employed utilizing the FLP-FRT system For inactivation of the expression of a Gene of Interest at a specific stage in development or a particular tissue, the coding region of the Gene of Interest is replaced by a cassette comprising the coding region flanked by LoxP sites. The LoxP sites are targets for the Cre recombinase. The resulting transgenic animal is crossed to another transgenic animal in which the Cre recombinase is expressed under the control of a spatially and/or temporally regulated promoter. When Cre expression is activated, the LoxP sites undergo recombination to excise the coding region of the Gene of Interest, resulting in tissues deficient for the Gene of Interest. Precursor cells from the transgenic animals comprising the Gene of Interest flanked by LoxP sites and optionally the Cre recombinase can be obtained for immortalization according to the methods described herein. If the precursor cells are obtained from a transgenic animal which does not comprise the Cre recombinase gene, the cells can be transfected with a Cre recombinase expression construct to induce the excision of the Gene of Interest.

Inducible gene disruption or expression can also be manipulated using the tetracycline repressor system. For inducible disruption of the Gene of Interest, the Tet operator can replace or be inserted into the native Gene of Interest regulatory elements, so that the expression of the Gene of Interest gene falls under the control of the tetracycline-controllable repressor (TetR), which can only repress transcription in the presence of tetracycline. Transgenic animals comprising the Tet promoter in the Gene of Interest gene are then crossed to animals which express TetR, and the expression of the Gene of Interest repressed by administering tetracycline to the animals. Precursor cells from the transgenic animals comprising the Tet promoter in the Gene of Interest and optionally the TetR under the control of an inducible promoter can be obtained for immortalization according to the methods described herein. If the precursor cells are obtained from a transgenic animal which does not comprise the TetR gene, the cells can be transfected with a TetR expression construct, and the culture contacted with tetracycline to inhibit expression of the Gene of Interest, as described in U.S. Pat. No. 5,922,927.

5.12 Genetic Engineering of Cells

The Immortalized cell populations can be genetically engineered to produce gene products beneficial upon transplantation of the genetically engineered cells to a subject. Such gene products include but re not limited to anti-inflammatory factors, e.g., anti-TNF, anti-IL-1, anti-IL-2, etc. Alternatively, the mesenchymal stem and progenitor cells can be genetically engineered to "knock out" expression of MHC in order to lower the risk of rejection. In addition, the cell populations can be genetically engineered for use in gene therapy to adjust the level of gene activity in a subject to assist or improve the results of transplantation or to treat a disease in caused by, for example, a deficiency in the recombinant gene. The cell populations are made recombinant by the introduction of a recombinant nucleic acid into the precursor cell or into the Immortalized or Differentiated cell population.

In its broadest sense, gene therapy refers to therapy performed by the administration of a nucleic acid to a subject. The nucleic acid, either directly or indirectly via its encoded protein, mediates a therapeutic effect in the subject. The present invention provides methods of gene therapy wherein a nucleic acid encoding a protein of therapeutic value (preferably to humans) is introduced into the precursor cells manipulated according to the methods of the invention, before or after manipulation and before or after immortalization, such that the nucleic acid is expressible by the precursor cells and/or their progeny, followed by administration of the recombinant cells to a subject.

The recombinant cells of the present invention can be used in any of the methods for gene therapy available in the art. Thus, the nucleic acid introduced into the cells may encode any desired protein, e.g. a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see Lundstrom, 1999, J. Recept. Signal Transduct. Res. 19:673-686; Robbins and Ghivizzani, 1998, Pharmacol. Ther. 80:35-47; Pelegrin et al., 1998, Hum. Gene Ther. 9:2165-2175; Harvey and Caskey, 1998, Curr. Opin. Chem. Biol. 2:512-518; Guntaka and Swamynathan, 1998, Indian J. Exp. Biol. 36:539-535; Desnick and Schuchman, 1998, Acta Paediatr. Jpn. 40:191-203; Vos, 1998, Curr. Opin. Genet. Dev. 8:351-359; Tarahovsky and Ivanitsky, 1998, Biochemistry (Mosc) 63:607-618; Morishita et al., 1998, Circ. Res. 2:1023-1028; Vile et al., 1998, Mol. Med. Today 4:84-92; Branch and Klotman, 1998, Exp. Nephrol. 6:78-83; Ascenzioni et al., 1997, Cancer Lett. 118:135-142; Chan and Glazer, 1997, J. Mol. Med. 75:267-282. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant precursor cells are used in gene therapy, a gene whose expression is desired in a subject is introduced into the precursor cells such that it is expressible by the cells and/or their progeny, and the recombinant cells are then administered in vivo for therapeutic effect.

Recombinant cell populations can be used in any appropriate method of gene therapy, as would be recognized by those in the art upon considering this disclosure. The resulting action of recombinant cell populations administered to a subject can, for example, lead to the activation or inhibition of a pre-selected gene in the subject, thus leading to improvement of the diseased condition afflicting the subject.

In this embodiment, the desired gene is introduced into the precursor cell or its progeny prior to administration in vivo of the resulting recombinant cell. Such introduction can be carried out by any method known in the art, including but not limited to transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g. Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the gene to the cell, so that the gene is expressible by the cell and preferably heritable and expressible by its cell progeny. Usually, the method of transfer includes the transfer of a selectable marker to the cells. The cells are then placed under selection to isolate those cells that have taken up and are expressing the transferred gene. Those cells are then delivered to a subject.

One common method of practicing gene therapy is by making use of retroviral vectors (see Miller et al., 1993, Meth. Enzymol. 217:581-599). A retroviral vector is a retrovirus that has been modified to incorporate a preselected gene in order to effect the expression of that gene. It has been found that many of the naturally occurring DNA sequences of retroviruses are dispensable in retroviral vectors. Only a small subset of the naturally occurring DNA sequences of retroviruses is necessary. In general, a retroviral vector must contain all of the cis-acting sequences necessary for the packaging and integration of the viral genome. These cis-acting sequences are:

a) a long terminal repeat (LTR), or portions thereof, at each end of the vector;

b) primer binding sites for negative and positive strand DNA synthesis; and c) a packaging signal, necessary for the incorporation of genomic RNA into virions.

The gene to be used in gene therapy is cloned into the vector, which facilitates delivery of the gene into a precursor cell by infection or delivery of the vector into the cell.

More detail about retroviral vectors can be found in Boesen et al. 1994, Biotherapy 6:291-302, which describes the use of a retroviral vector to deliver the mdr1 gene to HSCs in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are also of use in gene therapy. Adenoviruses are especially attractive vehicles for delivering genes to respiratory precursor cells. Adenoviruses can also be used to deliver genes to precursor cells from the liver, the central nervous system, endothelium, and muscle. Adenoviruses have the advantage of being capable of infecting non-dividing cells. Kozarsky and Wilson, 1993, Current Opinion in Genetics and Development 3:499-503 present a review of adenovirus-based gene therapy. Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234.

It has been proposed that adeno-associated virus (AAV) be used in gene therapy (Walsh et al., 1993, Proc. Soc. Exp. Biol. Med. 204:289-300). It has also been proposed that alphaviruses be used in gene therapy (Lundstrom, 1999, J. Recept. Signal Transduct. Res. 19:673-686).

Other methods of gene delivery in gene therapy include mammalian artificial chromosomes (Vos, 1998, Curr. Op. Genet. Dev. 8:351-359); liposomes (Tarahovsky and Ivanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

A desired gene can be introduced intracellularly and incorporated within host precursor cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, the desired gene recombinantly expressed in the precursor cell or its progeny to be introduced for purposes of gene therapy comprises an inducible promoter operably linked to the coding region, such that expression of the recombinant gene is controllable by controlling the presence or absence of the appropriate inducer of transcription.

In a preferred embodiment, the desired gene recombinantly expressed in the precursor cell or its progeny, is flanked by Cre sites. When the gene function is no longer required, the cells comprising the recombinant gene are subjected to Lox protein, for example be means of supplying a nucleic acid containing the Lox coding sequences functionally coupled to an inducible or tissue specific promoter, or by supplying Lox protein functionally coupled to a nuclear internalization signal. Lox recombinase functions to recombine the Cre sequences (Hamilton et al., 1984, J. Mol. Biol. 178:481-486), excising the intervening sequences in the process, which according to this embodiment contain a nucleic acid of a desired gene. The method has been used successfully to manipulate recombinant gene expression (Fukushige et al., 1992, Proc. Natl. Acad. Sci. USA 89:7905-7909). Alternatively, the FLP/FRT recombination system can be used to control the presence and expression of genes through site-specific recombination (Brand and Perrimon, 1993, Development 118:401-415).

5.13 Methods of Transplantation

The Immortalized and/or Differentiated cell populations, whether recombinantly expressing a desired gene or not, can be transplanted into a subject for the treatment of disease or injury or for gene therapy by any method known in the art which is appropriate for the type of stem cell being transplanted and the transplant site. HSCs or more differentiated derivatives can be transplanted intravenously, as can liver cells which will locate to the liver. Neural stem cells can be transplanted directly into the brain at the site of injury or disease.

In a preferred embodiment, the cell populations comprising Immortalized or Differentiated cells for transplantation are purified or at least highly enriched. Methods describing the purification and enrichment of cell populations (e.g., FACS, MACS, etc.) described for precursor cells in Section 5.4, supra, are applicable to the purification or enrichment of cell populations for transplantation.

In one embodiment, the transplantation of Immortalized or Differentiated cells is autologous. Autologous transplantation can be performed, for example, when the Immortalized or Differentiated cell has been genetically engineered to express a gene that is otherwise deficient in the subject. Autologous transplantation of Immortalized or Differentiated cells can be carried out to reconstitute in a subject a hematopoietic cell population that has been depleted by chemotherapy. Preferably, HSCs are isolated for immortalization according to the methods of the invention prior to the subject's exposure to chemotherapy, and the Immortalized or Differentiated cells transplanted back to the subject following exposure to chemotherapy.

In another embodiment, the transplantation of Immortalized or Differentiated cells is non-autologous. This embodiment is practiced, for example, when a subject's own cells are absent or too low in number to establish a culture, or the subject is too sick to undergo an explant procedure. Non-autologous transplantations are used preferably in conjunction with a method of suppressing rejection.

Methods of introduction include but are not limited to intradermal, intramuscular, intraperitoneal, intravenous, subcutaneous, intranasal, and epidural routes. The cell populations may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir.

In a specific embodiment, it may be desirable to administer the cell populations of the invention locally to the area in need of treatment; this may be achieved by, for example, and not by way of limitation, local infusion during surgery, topical application, e.g. in conjunction with a wound dressing after surgery, by injection, by means of a catheter, or by means of an implant, said implant being of a porous, non-porous, or gelatinous material, including membranes, such as sialastic membranes, or fibers.

By way of example, implantation of cells into the brain can be performed as follows. Implantation is done at three sites in the left putamen with a stereotactic technique (Lindvall et al., 1989, Arch. Neurol. 46:615). For each site, 20 µl of the dissociated cells is drawn into the instrument (outer diameter, 1.0 mm). The cells are injected along a 10, 12 and 14 mm linear tract, respectively, in either 2.5 µl portions for 15 to 20 seconds each. Between each injection there is a 2 minute delay, and the cannula is then retracted 1.5 to 1.7 mm. After the final injection, the cannula is left in situ for 8 minutes before being slowly withdrawn from the brain. After surgery the cell viability is assessed following the procedure of Brundin et al., 1985 (Brain. Res. 331:251).

In a preferred embodiment, the cell transplant is autologous. In another embodiment, the transplant is non-autologous. In a specific embodiment, the transplanted cells can be an organ or tissue type produced according to the methods of the invention.

The titer of stem cells transplanted which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances.

The subject is preferably an animal, including but not limited to animals such as cows, pigs, horses, chickens, cats, dogs, etc., and is preferably a mammal, and most preferably human.

5.14 Pharmaceutical Compositions

The invention provides methods of treatment by administration to a subject of a pharmaceutical (therapeutic) composition comprising a therapeutically effective amount of a recombinant or non-recombinant cell produced by the immortalizing and optionally differentiating a precursor cell according to the methods of the present invention. In a preferred aspect, the Immortalized or Differentiated cell is substantially purified.

The present invention provides pharmaceutical compositions. Such compositions comprise a therapeutically effective amount of an Immortalized cell, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, or emulsion.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

5.14.1 Pharmaceutical Kits

The invention also provides a pharmaceutical pack or kit comprising one or more containers filled with one or more of cell populations produced by the methods of the invention and/or reagents to prepare said cells, or with reagents for the genetic manipulation of the cells.

In a preferred embodiment, a kit of the invention comprises in one or more containers a one or more purified growth factors that promote proliferation but not differentiation of a precursor cell and a purified Notch agonist, which growth factors and Notch agonist are together effective to immortalize a precursor cell exposed to them in culture. Optionally, the kit further comprises in a separate container one or more purified growth factors that promote the differentiation of the precursor cell. Optionally, cell culture medium is also provided. Optionally associated with such container(s) can be a notice in the form prescribed by a governmental agency regulating the manufacture, use or sale of pharmaceuticals or biological products, which notice reflects approval by the agency of manufacture, use or sale for human administration.

Alternative embodiments for implementing the methods and producing the cells and animals of the present invention will be apparent to one of skill in the art and are intended to be comprehended within the accompanying claims. The following experimental examples are offered by way of illustration and not by way of limitation.

6 EXAMPLES

6.1 Soluble Delta-1 Requires Immobilization to Induce Notch Activation in C2 Myoblasts There are conflicting reports as to whether only cell-bound forms of Notch ligands can activate Notch receptors, or whether soluble forms are also capable of activating Notch (Wang et al., 1998, Neuron 21: 63-75; Qi et al., 1999, Science 283: 91-94). The ability of soluble ligand forms may depend on the nature of the Notch-ligand form and the cell system under evaluation To evaluate requirements for Delta-induced Notch signaling, soluble forms of Delta-1 were prepared, both a monomeric form in which the entire extracellular domain of Delta-1 was fused to myc epitopes (Delta$^{ext-myc}$) and a dimeric form in which the extracellular domain was fused to the Fc portion of human IgG-1 (Delta$^{ext-IgG}$). To present these ligands in immobilized form, Delta$^{ext-myc}$ or Delta$^{ext-IgG}$ was attached to the plastic surface of tissue culture wells by binding to the 9E10 anti-myc tag antibody, or to anti-human IgG1 Fc domain antibody, respectively, that had previously been adsorbed to the plastic.

The effects of these ligand forms on C2 myoblast differentiation, where Notch activation has been shown to inhibit myotube formation, were assessed. When C2 myoblasts were plated on a plastic surface bearing immobilized Delta$^{ext-myc}$ or Delta$^{ext-IgG}$, differentiation was inhibited, indicative of Notch activation. In contrast, neither Delta$^{ext-myc}$ nor Delta$^{ext-IgG}$ in solution (non-immobilized) inhibited C2 myoblast differentiation, indicating that non-immobilized truncated Delta even in dimeric form does not activate Notch. Furthermore, both Delta$^{ext-myc}$ and Delta$^{ext-IgG}$ in solution blocked the effect of immobilized Delta. These results indicate that truncated forms of Delta-1 function as Notch agonists when immobilized on a plastic surface, and that non-immobilized forms can potentially be used as inhibitors of ligand-induced signaling. Both immobilized and non-immobilized ligands, however, induced proteolytic cleavage of Notch-1 as indicated by increased formation of the truncated, presumably activated 115 kD form of the intracellular domain.

6.2 Overexpressed Notch-1 Intracellular Domain Inhibits Differentiation of Hematopoietic Precursors To characterize the effects of Notch-1 signaling on hematopoiesis, lin$^-$Sca-1$^+$c-kit$^+$ murine marrow cells were infected with either a retrovirus encoding activated Notch-1 fused to green fluorescent protein (GFP) (ICT in FIG. 2) or a control virus lacking the Notch-1 sequences but including GFP (R1, FIG. 2). This retrovirus construct contains the major portion of the Ram domain and encodes an IRES domain and GFP, facilitating detection of activated Notch-1-expressing cells.

Isolated precursors (lin$^-$Sca-1$^+$c-kit$^+$) from C57/BL6 mice were incubated with IL-6, IL-11, SCF and Flt-3L for 48 hr before addition of virus-containing supernatant. After 24 hr, spent virus was removed and fresh virus was added for an additional 24 hr. After infection, GFP-expressing cells were isolated by flow microfluorometry, and $2 \times 10^4$ cells were cultured with c-kit ligand, IL-6, IL-11, and Flt-3L.

At 5 days post-infection, the number cells from cultures containing GFP-expressing cells infected with the control retrovirus had increased approximately 30-fold. Cytocentrifuge preparations stained with Wright-Geimsa revealed that the majority of the cells had differentiated into granulocytes or macrophages (data not shown). Flow cytometry studies indicated that 63% of the cells expressed the granulocyte-associated antigen, Gr-1, 6% expressed the macrophage-associated antigen, F4/80, and only 12% continued to express Sca-1 (R1 in FIG. 3).

Cultures containing GFP$^+$, activated Notch-1-expressing cells had fewer cells than control cultures, but had still increased in number about 21-fold. However, in contrast to control cultures, most of the cells were undifferentiated blasts as detected in cytocentrifuge preparations (not shown). Flow cytometry indicated that only 9.5% of the cells expressed GR-1, 4% expressed F4/80, whereas 77% continued to express Sca-1 (ICT in FIG. 3). To assess the effect of activated Notch-1 on the precursor cell types HPP-mix and CFU-C, colony growth was assessed in semi-solid medium. Numbers of HPP-mix and CFU-C were 100-fold and 2-fold greater, respectively, in cultures containing Notch-1 intracellular domain-expressing cells than in cultures containing cells expressing the control vector (FIG. 4).

These activated Notch-1-expressing cells have continued to proliferate in culture for 5 months in 100 ng/ml each of SCF, IL-6, and Flt-3L, and 10 ng/ml IL-11, with a doubling time of about 18 hr. The continuous growth of activated Notch-1-expressing cells was optimal in the four-cytokine combination but slower in 100 ng/ml of SCF (doubling time of 24 hr), and undetectable in 10 ng/ml of SCF or IL-11, or 100 ng/ml of IL-6, Flt-3L, GM-CSF, or G-CSF. Cells growing in the four-cytokine combination all expressed Sca-1, and a subset (38%) expressed CD25 (low-affinity IL-2 receptor, IL-2Rα), c-kit, and CD44, likely indicating early T lineage commitment. None of the cells expressed CD4 or CD8, or CD19 antigens, associated with mature T and B cell differentiation, respectively, or antigens associated with myeloid differentiation, including Ter119, GR-1 and F4/80. Continued expression of the intracellular domain of Notch-1 was confirmed by Western analysis (data not shown).

Thus, in the presence of the four cytokines, Notch-1-induced signaling permitted the expansion of undifferentiated cells, as well as cells with a phenotype suggestive of early T cell development. In subsequent studies of these activated Notch-1 expressing cells, i) the effect of cytokines on their differentiation, and ii) their in vivo repopulating ability were analyzed. In addition, iii) cloned cell lines have been established.

6.2.1 Activated Notch-1 Expressing Cells Proliferate in Undifferentiated Form or Differentiate Along the Myeloid or Lymphoid Pathway Depending on Cytokines Present in the Cultures The effect of cytokines known to induce myeloid or lymphoid differentiation on the phenotype of the activated Notch-1-expressing cells was determined. Cells that had been maintained in culture for four months in the four-cytokine combination were incubated for five days in 10 ng/ml SCF and 100 ng/ml of either GM-CSF or IL-7. Incubation with SCF and GM-CSF led to expression of Gr-1 and F4/80 in 39% and 22% of the cells, respectively, as compared with <1% in the four-cytokine combination, whereas the proportion of cells that expressed CD25 decreased from 38% to 20%. In contrast, the portion of CD25$^+$ cells in cultures containing SCF and IL-7 increased to 85%. Thus, depending on the cytokine milieux, undifferentiated Notch-1-expressing cells can express a phenotype indicative of either myeloid or early lymphoid differentiation, and thus may have the properties of a pluripotent lymphoid/myeloid precursor cell.

6.2.2 Activated Notch-1-Expressing Precursors Repopulate Both the Lymphoid and Myeloid Lineages In Vivo in a Short-Term Assay To assess the effect of activated Notch-1 on in vivo repopulating cells, $10^6$ cells from cultures that had been maintained for 36 days after retroviral infection were administered intravenously to irradiated (1000 cGy) congenic C57/BL6 Ly 5.1 recipients along with $10^5$ normal marrow cells from congenic Ly 5.1 mice to ensure survival. At this time, control cultures had extinguished and were no longer available for in vivo evaluation. Eleven days later, flow cytometric analysis of peripheral blood cells revealed repopulation of the T cell lineage, as indicated by CD4$^+$ and CD8$^+$ GFP-expressing cells, and repopulation of the myeloid lineages as indicated by Gr-1$^+$ and Mac-1$^+$ GFP-expressing cells (FIG. 5). Similar results were obtained following transplantation of Notch-1 expressing cells 60 days post-infection.

Repopulating ability was proportional to the number of transplanted cells since a lower percentage of donor cells was observed in mice that had received $10^5$ cells (data not shown). However, as anticipated, T cells expressing the intracellular domain of Notch-1 also gave rise to leukemic cells, leading to death of the animals and preventing assessment of long-term repopulation. Nonetheless, these experiments demonstrate Notch-1-induced enhancement of the generation of hematopoietic precursors, including at least short-term in vivo repopulating cells.

6.2.3 Establishment of Clonal, Cytokine-Dependent Notch-1-Expressing Cell Lines Southern blot analysis of continuously growing activated Notch-1-expressing cells demonstrated multiple integration sites, indicative of non-clonal growth. Because the observed lymphoid and myeloid differentiation might have resulted from different clonal populations, limiting dilution cloning was used to establish three clonal cell lines, each with a single, unique viral integration site. Cells from each clone have grown continuously for more than three months in the four-cytokine combination and express the intracellular domain of Notch-1 as confirmed by Western analysis (data not shown). Like the multi-clonal parental cells, the cloned cells cultured in the presence of cytokines supporting myeloid or lymphoid differentiation also showed enhanced expression of myeloid associated (Gr-1 and F4/80) or lymphoid associated (CD25, Thy-1) antigens. For example, cells from one clone, clone 10, cultured in the four cytokine combination expressed Sca-1 (>97%), and a portion expressed CD25 (18%) and c-kit (70%), while few cells expressed Gr-1 (<5%). However, after five days in the presence of 10 ng/ml SCF and 100 ng/ml GM-CSF, a greater percentage expressed Gr-1 (44%), while fewer cells expressed Sca-1 (31%), CD25 (<1%) and c-kit (8%). In contrast, after incubation with 10 ng/ml of SCF and 100 ng/ml IL-7, the majority of cells expressed CD25 (77%) and c-kit (94%), while only 2% expressed Gr-1. These data suggest the lymphoid and myeloid potential of these cells, and thus their derivation from a pluripotent precursor.

6.2.4 Immobilized Delta-1 Extracellular Domain Promotes Expansion of Undifferentiated Hematopoietic Cells Exposure of isolated murine hematopoietic precursors exposed to human Jagged-1, whether expressed by cells or in a soluble form bound to a solid phase, led to increased numbers of HPP-mix (Varnum-Finney et al., 1998, Blood 91:4084-4091). The effect of Delta-1 on isolated hematopoietic precursors in conjunction with IL-6, IL-11, SCF and Flt-3L was evaluated. A soluble form of the Delta-1 extracellular domain fused with human $IgG_1$ Fc domain ($Delta^{ext-IgG}$) and a control Jagged-1 signal peptide fused with human $IgG_1$ Fc domain. $Delta^{ext-IgG}$ immobilized on plastic inhibited C2 myoblast differentiation, indicating activation of Notch.

Incubation of $lin^-Sca-1^+c-kit^+$ cells for 13 days with immobilized $Delta^{ext-IgG}$ or with immobilized control IgG fusion construct in the presence of IL-6, IL-11, SCF and Flt-3L generated similar numbers of cells in each culture, with an approximate $10^6$-fold increase. In control cultures, most of the cells had differentiated into granulocytes as indicated by Wright-Geimsa-stained cytocentrifuge slides (not shown) and by flow cytometry studies which revealed Gr-1 expression in 92% of the cells, whereas <1% still expressed Sca-1 (FIG. 6). In contrast, approximately 50% of the cells incubated with Delta-1 were undifferentiated blast cells, and 52% of the cells continued to express Sca-1, while only 48% expressed GR-1. In addition, by day 21 of culture, 19% of the ligand-exposed cells expressed CD25 (not shown).

In four experiments to assess colony-forming activity, numbers of CFU-C increased 5 to 13-fold and numbers of HPP-mix increased two- to 186-fold in cultures containing immobilized $Delta^{ext-IgG}$ compared to control cultures (FIG. 7). Additional studies showed that non-immobilized ligand had no effect on differentiation or on the numbers of colony-forming cells, but it was able to inhibit effects of immobilized ligand, consistent with results obtained with C2 cells.

6.3 Delta-1 Enhances Generation of Cells with In Vivo Repopulating Activity in a Short-Term Assay $10^3$ $lin^-Sca-1^+c-kit^+$ cells from C57/BL6 (Ly5.2) mice were incubated for 13 days with SCF, IL-6, IL-11 and Flt-3L with either immobilized $Delta^{ext-IgG}$ or $Control^{IgG}$. Cells were replated in fresh culture wells on day 6 and day 10 to maintain density, and after 13 days, the total number of immortalized cells derived from the initial $10^3$ cells were then injected into 1000-cGy irradiated, congenic C57/BL6 (Ly5.1) recipients along with $10^5$ competing Ly5.1 cells. A total of seven mice were injected for each culture condition.

After 1 month, an increase was observed in short-term reconstitution by cells incubated with Delta-1 compared to control in each of two experiments (Table 1). The repopulating, Ly5.2 cells from Delta-1-containing cultures in experiments 1 and 2 consisted of 19% and 92% $CD19^+$ cells, 58% and 10% $Thy-1^+$ cells, and 5% and 8% $Gr-1^+$ cells, respectively, suggesting enhancement of predominantly lymphoid, but also myeloid repopulation.

TABLE 1

In vivo reconstitution at one month by $lin^-$ $Sca-1^+$ $c-kit^+$ (Ly5.2) cells following 13 day ex vivo culture with $Delta^{ext-IgG}$ or $Control^{IgG}$ (% Ly 5.2 donor cells +/- s.e.m.).

|  | $Delta^{ext-IgG}$ | $Control^{IgG}$ |
| --- | --- | --- |
| Experiment 1 | 6.9% +/- 0.6 | 0% +/- 0.7 |
| Experiment 2 | 11.8% +/- 3.3 | 1.3% +/- 0.2 |

6.4 Synergistic Effect of Notch Ligand and ATRA on Hematopoietic Precursors

ATRA enhances the generation of precursor cells, including HPP-mix, and maintains or immortalizes long-term repopulating cells from $lin^-Sca-1^+c-kit^+$ cells (Purton et al., 1999, Blood 94:483-495; Purton et al., 2000, Blood 95:470-477). The effect of combining ATRA and immobilized Delta-1 on $lin^-Sca-1^+c-kit^+$ cells was evaluated. After 13 days of culture, comparable numbers of cells were found in cultures containing Delta-1, ATRA, or both. However, CFU-C and HPP-mix were increased 5- and 157-fold, respectively, in cultures containing both Delta-1 and ATRA compared to cultures containing Delta-1 or ATRA alone (FIG. 7). After 20 days of culture, comparable numbers of cells were found in cultures containing Delta-1, ATRA, or both. In all three conditions, there were 10 fold more cells than in cultures with $Control^{IgG}$. Further there was a substantially greater number of HPP-mix in cultures with both Delta-1 and ATRA than in Delta-1 or ATRA alone (FIG. 8), whereas the presumably more mature CFU-C were increased in number in both ATRA and ATRA and ligand containing cultures. In addition, after 20 days of culture, a lower proportion of cells expressed CD25 (8%) compared to cells in cultures with Delta-1 alone (19%). These studies suggest synergistic effects of Delta-1 and ATRA on the generation of colony-forming cells, and possibly an inhibition of lymphoid differentiation. Transplantation studies are underway to determine whether there is also a synergistic effect on in vivo repopulating cells Overall, the Examples presented herein indicate that activation of the Notch receptor pathway inhibits differentiation by hematopoietic precursor cells and promotes the expansion of the $Sca-1^+$ population, of colony-forming precursor cells, and of short-term in vivo repopulating cells. The data further indicate that Notch-mediated effects are modulated by extrinsic factors such as cytokines.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications, including patents and scientific literature, are cited herein, the disclosures of which are incorporated by reference in their entireties for all purposes.

What is claimed is:

1. A method for producing an immortalized hematopoietic stem cell population comprising culturing a non-immortalized hematopoietic stem cell in the presence of (a) an immobilized fibronectin or a fragment thereof; (b) an immobilized Notch agonist comprising an extracellular, Notch-interacting domain of a Delta, a Jagged, or a Serrate protein; and (c) Stem cell factor (SCF) in combination with two or more of Flt-3 ligand (Flt-3), Interleukin-6 (IL-6), Interleukin-3 (IL-3), Interleukin-11 (IL-11), thrombopoietin (TPO), Granulocyte-macrophage colony stimulating factor (GM-CSF), or granulocyte colony stimulating factor (G-CSF); wherein said combination of (a), (b), and (c) is together effective to maintain a proliferating hematopoietic stem cell population comprising a majority of cells that do not terminally differentiate for a time period beyond which hematopoietic stem cells not in the presence of (a), (b), and (c) stop proliferating and/or die while exposed to them in culture, thereby producing an immortalized hematopoietic stem cell population.

2. The method of claim 1, wherein the hematopoietic stem cell is obtained from bone marrow, umbilical cord blood, placental blood, or Wharton's jelly.

3. The method of claim 1, wherein the hematopoietic stem or progenitor cell is obtained from fetal or neonatal blood.

4. The method of claim 1 wherein said time period is at least four weeks, at least five weeks, or at least six weeks.

5. The method of claim 1 wherein said immortalized precursor hematopoietic stem cell population is a clonal cell population.

6. The method of claim 5 which further comprises using limited dilution cloning to isolate a clonal cell line.

7. The method of claim 1 wherein the hematopoietic stem cell is a mammalian cell.

8. The method of claim 7, wherein the murine mammalian cell is a murine marrow hematopoietic precursor that is lin⁻ Sca-1⁺ c-kit⁺.

9. The method of claim 1, wherein the Notch agonist is an extracellular, Notch-interacting domain of a Delta protein.

10. The method of claim 9, wherein the Delta protein is $Delta^{ext-IgG}$.

11. The method of claim 7, wherein the hematopoietic stem cell is a human cell.

12. The method of claim 1 wherein the non-immortalized hematopoietic stem cells are frozen prior to culturing or the immortalized hematopoietic stem cell population is frozen subsequent to culturing.

13. The method of claim 1, wherein the Notch agonist is in dimeric form.

14. The method of claim 1, wherein the fragment of fibronectin is CH-296.

15. The method of claim 1, wherein the two or more growth factors in combination with SCF are IL-6, IL-11, or Flt-3L.

16. The method of claim 1, wherein the two or more growth factors in combination with SCF are Flt-3L, TPO, IL-6, or IL-3.

* * * * *

UNITED STATES PATENT AND TRADEMARK OFFICE
CERTIFICATE OF CORRECTION

PATENT NO. : 8,071,377 B2
APPLICATION NO. : 12/173185
DATED : December 6, 2011
INVENTOR(S) : Bernstein et al.

Page 1 of 1

It is certified that error appears in the above-identified patent and that said Letters Patent is hereby corrected as shown below:

In the Claims

| COLUMN | LINE | ERROR |
|---|---|---|
| 57 (Claim 3) | 30 | delete "or progenitor" |
| 58 (Claim 5) | 1-2 | delete "precursor" |
| 58 (Claim 8) | 8 | delete "murine" |

Signed and Sealed this
Eighth Day of October, 2013

Teresa Stanek Rea
*Deputy Director of the United States Patent and Trademark Office*